(12) United States Patent
Hanebuchi

(10) Patent No.: US 8,777,410 B2
(45) Date of Patent: Jul. 15, 2014

(54) FUNDUS PHOTOGRAPHING APPARATUS WITH WAVEFRONT COMPENSATION

(75) Inventor: Masaaki Hanebuchi, Aichi (JP)

(73) Assignee: Nidek Co., Ltd., Gamagori (JP)

( * ) Notice: Subject to any disclaimer, the term of this patent is extended or adjusted under 35 U.S.C. 154(b) by 137 days.

(21) Appl. No.: 13/600,793

(22) Filed: Aug. 31, 2012

(65) Prior Publication Data

US 2013/0057826 A1     Mar. 7, 2013

(30) Foreign Application Priority Data

Sep. 2, 2011   (JP) ................................. 2011-191292
Sep. 2, 2011   (JP) ................................. 2011-191294

(51) Int. Cl.
*A61B 3/10*     (2006.01)

(52) U.S. Cl.
USPC .......................................... 351/206; 351/208

(58) Field of Classification Search
USPC ........................... 351/208, 206, 246, 205, 221
See application file for complete search history.

(56) References Cited

U.S. PATENT DOCUMENTS

| | | | |
|---|---|---|---|
| 5,777,719 | A | 7/1998 | Williams et al. |
| 2006/0170865 | A1 | 8/2006 | Hirohara et al. |
| 2008/0259273 | A1 | 10/2008 | Williams et al. |
| 2010/0277692 | A1* | 11/2010 | Mukai et al. .................. 351/208 |

FOREIGN PATENT DOCUMENTS

| | | |
|---|---|---|
| EP | 2 322 082 A1 | 5/2011 |
| JP | A-2001-507258 | 6/2001 |

OTHER PUBLICATIONS

Feb. 15, 2013 Search Report issued in European Patent Application No. EP 12 18 2454.4.

\* cited by examiner

*Primary Examiner* — Hung Dang
(74) *Attorney, Agent, or Firm* — Oliff PLC

(57) ABSTRACT

A fundus photographing apparatus with wavefront compensation, includes: a fundus photographing optical system for capturing a fundus image by receiving a reflected light from fundus of an examinee's eye; a wavefront compensation device placed in an optical path of the fundus photographing optical system to compensate a wavefront aberration of the examinee's eye by controlling an incident light wavefront; a wavefront aberration detection optical system for projecting a measurement light on the fundus of the examinee's eye to detect a reflected light of the measurement light from the fundus using a wavefront sensor; and a controller for controlling an effective region formed on the wavefront compensation device so as to correct a difference between the effective region formed on the wavefront compensation device where an aberration correction control is effective and a wavefront measurement region of the wavefront aberration detection optical system where the wavefront aberration is measured.

17 Claims, 14 Drawing Sheets

(a)

(b)

FUNDUS PHOTOGRAPHING APPARATUS WITH WAVEFRONT COMPENSATION

CROSS-REFERENCE TO RELATED APPLICATIONS

This application is based upon and claims the benefit of priority from the prior Japanese Patent Applications Nos. 2011-191292, filed Sep. 2, 2011, and 2011-191294, filed Sep. 2, 2011, the entire contents of which are incorporated herein by reference.

BACKGROUND OF THE INVENTION

1. Field of the Invention

The invention relates to a fundus photographing apparatus with wavefront compensation configured to photograph a fundus image of an examinee's eye with wavefront aberration of the examinee's eye having being corrected.

2. Related Art

So far was disclosed an apparatus configured to detect wavefront aberration of an eye using a wavefront sensor such as a Shack-Hartmann sensor and control a wavefront compensation device based on a detection result thereby obtained to capture a wavefront-compensated fundus image on a cellular level (for example, see PCT Application National Publication No. 2001-507258). On the wavefront sensor is preset a given effective region where the aberration is correctable by the wavefront compensation device. Then, the aberration is compensated based on an aberration detection result of a Hartmann image within the effective region in all of Hartmann images reflected from a fundus and received through a pupil. The apparatus thus configured, after an examinee's eye and the apparatus are positionally aligned to each other, repeatedly detects the wavefront aberration of the eye and performs the wavefront compensation control based on the detection result.

SUMMARY OF THE INVENTION

Problems to be Solved by the Invention

Conventionally, an effective region provided in a wavefront compensation device has a fixed size (for example, $\phi=5.5$ mm). On the other hand, pupils of different examinees naturally have different sizes, and the Hartmann images received through the pupils are accordingly received in different sizes. Depending on the size of the examinee's pupil, therefore, there may be generated a difference between the Hartmann image size and the effective region size, adversely affecting the aberration detection.

In the case where the examinee's pupil has a diameter larger than the effective region size (for example, $\phi=6.5$ mm), of all of incident lights entering the wavefront compensation device, the effective region can only receive light fluxes limited to a partial area (for example, $\phi=5.5$ mm of the effective region). Any other incident lights are reflected toward a photodetector with their wavefronts uncompensated. Of all of fundus reflected lights passing through a pupil region (region of $\phi=6.5$ mm), the fundus reflected lights in a region of $\phi=5.5$ mm to $\phi=6.5$ mm fail to have their aberrations corrected. Therefore, any information of the region of $\phi=5.5$ mm to $\phi=6.5$ mm does not serve the purpose of capturing an image having a high resolving power, making it difficult to capture such an image.

In the case where the examinee's pupil has a diameter smaller than the effective region size (for example, $\phi=5.0$ mm), the whole incident lights to the wavefront compensation device still fail to fulfill the effective region, resulting in the failure of aberration detection in any part of the region where the Hartmann image is not formed. In the event that the wavefront measurement data is thus partly missing, it is not possible to obtain the whole wavefront information, failing to correctly measure the wavefront aberration. As a result of the wavefront compensation control based on the detection result thus obtained, the wavefront compensation device is controlled based on an amount of aberration compensation wrongly measured. The fundus reflected lights passing through the pupil region (region of $\phi=5.0$ mm) do not penetrate through a partial area from $\phi=5.0$ mm to $\phi=5.5$ mm of the effective region ($\phi=5.5$ mm), where the aberration detection is not possible. As a result, the aberration cannot be optimally corrected, and the apparatus is unable to capture a fundus image with a good image quality where the wavefront aberration has been corrected.

Another problem is that an obtained fundus image may have a poor image quality in the case where the examinee's eye is not fixated long enough after the positional alignment of the examinee's eye and the apparatus.

FIG. 12A illustrates a result of light reception obtained by the wavefront sensor in the event of a fixation disparity. An effective region 62 of the wavefront compensation device is set on the wavefront sensor. In a region S where a Hartmann image 61 is not formed, no wavefront condition is detected. In the event that the wavefront measurement data is thus partly missing (see FIG. 12A), it is not possible to obtain the whole wavefront information, failing to correctly measure the wavefront aberration in the wavefront correcting region. As a result of the wavefront compensation control based on the detection result thus obtained, the wavefront compensation device is controlled based on an amount of aberration compensation wrongly measured.

At the occurrence of any fixation disparity, an examiner has to suspend the measuring operation to positionally realign a jaw rest and a forehead rest. Thus, the examiner needs to keep in mind such a possible positional realignment, which is burdensome to the examiner.

To solve the above conventional technical problems, the invention has a purpose to provide a fundus photographing apparatus with wavefront compensation wherein a fundus image with a good image quality can be smoothly captured with wavefront aberration thereof having been corrected.

Means of Solving the Problems

To achieve the above purpose, one aspect of the invention provides a fundus photographing apparatus with wavefront compensation, including: a fundus photographing optical system for capturing a fundus image by receiving a reflected light from fundus of an examinee's eye; a wavefront compensation device placed in an optical path of the fundus photographing optical system to compensate a wavefront aberration of the examinee's eye by controlling an incident light wavefront; a wavefront aberration detection optical system for projecting a measurement light on the fundus of the examinee's eye to detect a reflected light of the measurement light from the fundus using a wavefront sensor; and a controller for controlling an effective region formed on the wavefront compensation device so as to correct a difference between the effective region formed on the wavefront compensation device where an aberration correction control is effective and a wavefront measurement region of the wavefront aberration detection optical system where the wavefront aberration is measured.

DESCRIPTION OF EMBODIMENTS

Figure 1:
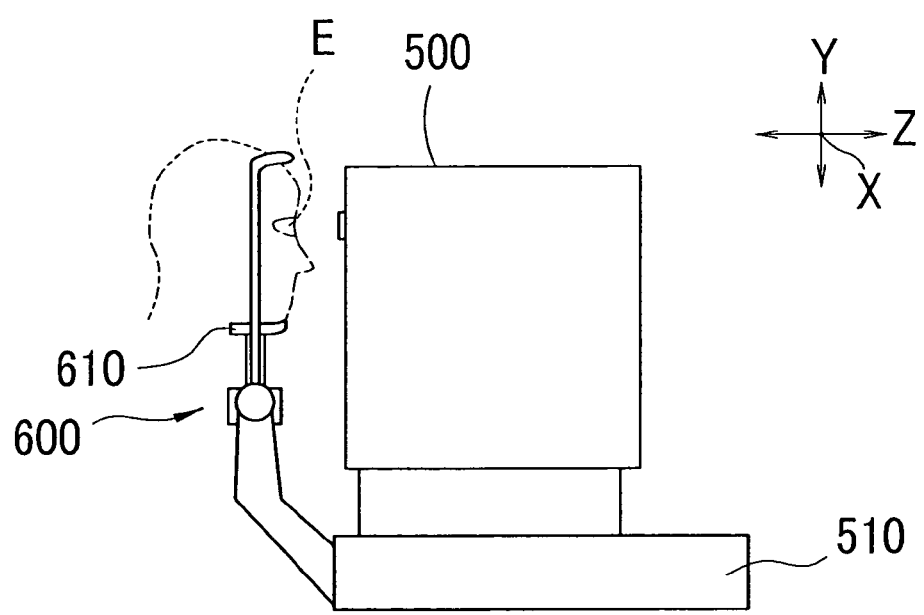
FIG. 1 illustrates an external appearance of a fundus photographing apparatus in an embodiment.

Hereinafter, embodiments according to the present invention are described in detail. FIG. 1 illustrates an external appearance of a fundus photographing apparatus according to embodiments of the invention. The apparatus includes a base table 510, a face support unit 600, and a photographing unit 500. The face support unit 600 is attached to the base table 510. The photographing unit 500 has optical systems housed therein, which will be described later. The photographing unit 500 is provided on the base table 510. The face support unit 600 is provided with a jaw rest 610. The jaw rest 610 is moved by manipulating a jaw rest driver not illustrated in the drawing to right and left (X direction), upward and downward (Y direction), and forward and backward (Z direction) relative to a base portion of the face support unit 600.

Figure 2:
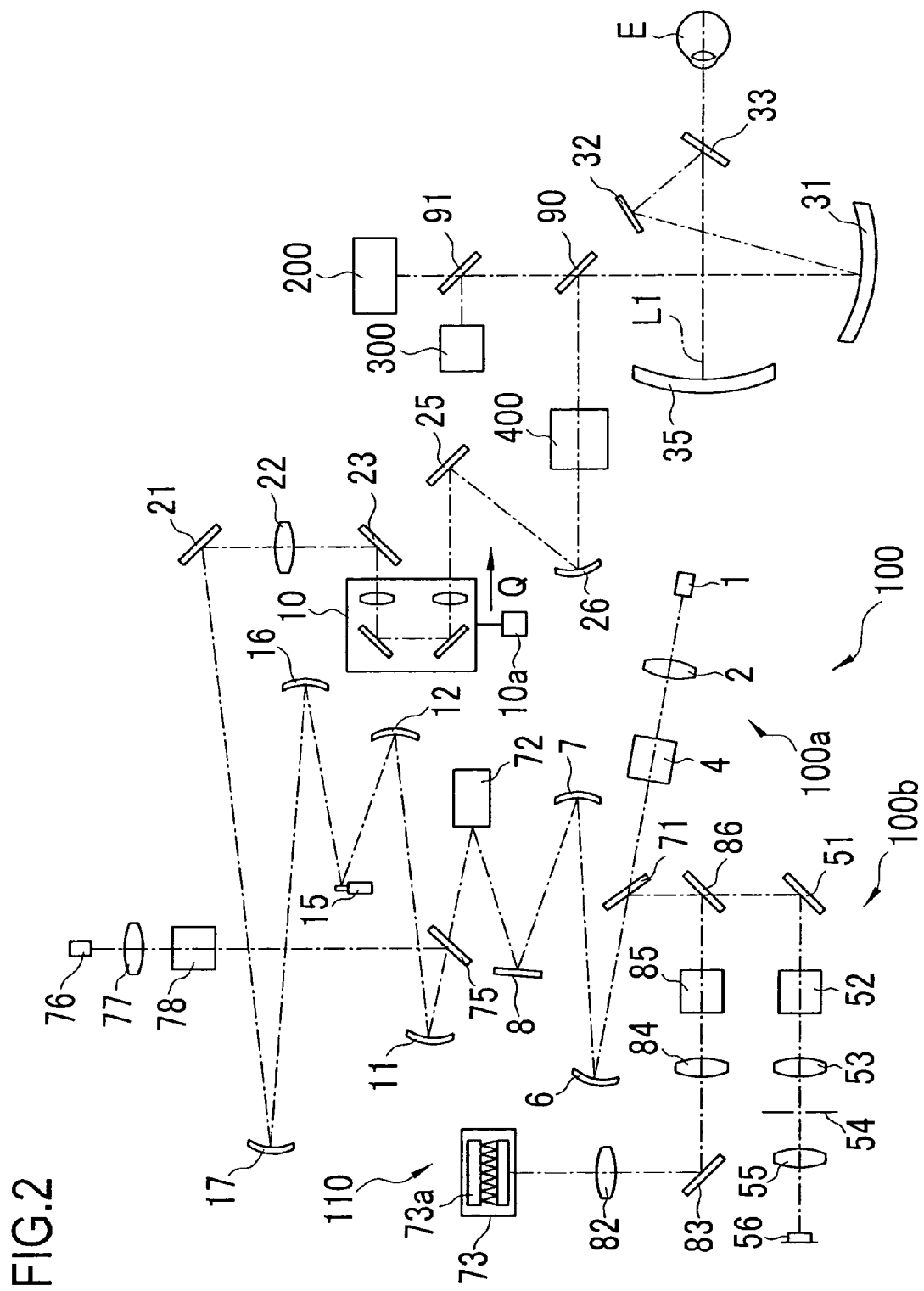
FIG. 2 is a schematic diagram to show an optical system of the fundus photographing apparatus in the embodiment.

FIG. 2 is a schematic diagram to show the optical systems provided in the fundus photographing apparatus according to the embodiments. The main structural elements of the fundus photographing apparatus according to the embodiments are; a fundus photographing optical system 100, a wavefront aberration detection optical system (hereinafter, referred to as an aberration detection optical system) 110, aberration compensation units 10 and 72, a second photographing unit 200, and a tracking unit (position detector) 300.

The fundus photographing optical system 100 receives a light reflected from fundus of an examinee's eye E to capture a fundus image of the examinee's eye. The aberration detection optical system (aberration measurement optical system) 110 is provided with a wavefront sensor 73. The aberration detection optical system 110 projects a measurement light on the fundus of the examinee's eye and receives (detects) the reflected light from the fundus using the wavefront sensor 73 as an index pattern image. The aberration compensation units 10 and 72 are provided in the fundus photographing optical system 100 to correct an aberration of the examinee's eye. To define a photographing position where the fundus image is captured by the fundus photographing optical system 100 (hereinafter, described as a first fundus image), the second photographing unit 200 obtains an observation image of the fundus (hereinafter, referred to as a second fundus image).

The fundus photographing optical system 100 photographs the fundus of the examinee's eye E with a high resolution (a high resolving power) by a high magnifying power. The main structural elements of the aberration compensation unit are; a visibility correction unit 10 which corrects a low-order aberration of the examinee's eye (visibility: for example, spherical degree), and a high-order aberration compensation unit (wavefront compensation device) 72 which corrects a high-order aberration of the examinee's eye.

The fundus photographing optical system 100 includes a first illumination optical system 100a which irradiates an illumination light (illumination light flux) on the examinee's eye E to two-dimensionally illuminate the fundus, a first photographing optical system 100b which receives a reflected light of the illumination light irradiated on the fundus (reflected light flux) to obtain the first fundus image, and the aberration compensation unit 72. The fundus photographing optical system 100 is, for example, a scanning laser ophthalmoscope where a confocal optical system is used.

The first illumination optical system 100a has a light source 1 (first light source) and a scan unit 15. The light source 1 emits illumination light in near infrared region that is hardly visually recognized by the examinee's eye. This illumination light is emitted to illuminate the fundus. The light source 1 used in the embodiments is an SLD (Super Luminescent Diode) light source providing a wavelength of 840 nm. The light source is not necessarily limited thereto and may be, for example, a semiconductor laser as far as a highly-convergent spot light is emitted therefrom. The scan unit 15 scans the fundus horizontally (X direction) using the illumination light (spot light) irradiated thereon.

First, the first illumination optical system 100a is described. The first illumination optical system 100a includes, in an optical path from the light source 1 to the fundus; a lens 2, a polarization beam splitter (PBS) 4, a concave mirror 6, a concave mirror 7, a planar mirror 8, the wavefront compensation device 72, a concave mirror 11, a concave mirror 12, the scan unit 15, a concave mirror 16, and a concave mirror 17. Further provided are; a planar mirror 21, a lens 22, a planar mirror 23, the visibility correction unit 10, a planar mirror 25, a concave mirror 26, a deflection unit 400, a dichroic mirror 90, a concave mirror 31, a planar mirror 32, a planar mirror 33, and a concave mirror 35. The visibility correction unit 10 includes a planar mirror and a lens. The deflection unit 400 scans the fundus vertically (Y direction) using the illumination light emitted from the light source 1 and irradiated on the fundus. Further, the deflection unit 400 corrects a scanning position of the illumination light two-dimensionally irradiated. The dichroic mirror 90 directs an optical path of the second photographing unit 200 to be substantially coaxial with that of the first illumination optical system 100a.

The illumination light emitted from the light source 1 passing through the lens 2 turns to a collimated light, entering the PBS 4. According to the embodiments, the illumination light having transmitted through the PBS 4 is a light flux including an S-polarized light component alone. The illumination light transmitting through the PBS 4 further passes through a beam splitter (BS) 71. The illumination light is then reflected by the concave mirror 6, concave mirror 7, and planar mirror 8 to enter the wavefront compensation device 72. The illumination light reflected by the wavefront compensation device 72 passes through a BS 75. The illumination light is then reflected by the concave mirror 11 and the concave mirror 12 and then directed toward the scan unit 15.

The scan unit 15 scans the fundus in the X direction using the illumination light irradiated thereon. The scan unit 15 according to the embodiments has a resonant mirror serving as a deflection member which deflects the illumination light horizontally (X direction) on the fundus for scan, and a drive unit which drives the mirror. The illumination light transmitting through the scan unit 15 is reflected by the concave mirror 16, concave mirror 17, and planar mirror 21 to be converged on the lens 22. Then, the illumination light is reflected by the planar mirror 23. The illumination light then passes through the visibility correction unit 10, and then is reflected by the planar mirror 25 and the concave mirror 26 and directed toward the deflection unit 400. The visibility correction unit 10 has a drive unit 10a, wherein an optical path length is changeable when the planar mirror and lens are moved in the direction illustrated with an arrow Q in FIG. 2. The visibility correction unit 10 thus characterized serves as a visibility corrector. The visibility correction unit 10 may include a drive unit and a prism movable in the direction of an optical axis when driven by the drive unit.

The deflection unit 400 scans the fundus in the X and Y directions using the illumination light irradiated thereon. According to the embodiments, the deflection unit 400 includes two galvano mirrors which are a galvano mirror for X scan and a galvano mirror for Y scan. A function of the deflection unit 400 is to further deflect the illumination light transmitting through the scan unit 15 by a predetermined amount in the X and Y directions. The illumination light transmitting through the deflection unit 400 is reflected by the dichroic mirror 90, concave mirror 31, planar mirror 32, planar mirror 33, and concave mirror 35 to converge on the fundus of the examinee's eye E so that the fundus is two-dimensionally scanned by the scan unit 15 and the deflection unit 400.

The dichroic mirror 90 transmits therethrough light fluxes from the second photographing unit 200 and the tracking unit 300 described later and reflects light fluxes from the light source 1 and a light source 76 described later. The light emission ends of the light source 1 and the light source 76 are located at positions conjugate with the fundus of the examinee's eye E. These optical devices constitute the first illumination optical system 100a which two-dimensionally irradiates the illumination light on the fundus.

The tracking unit 300 detects an aging variation of displacement of the examinee's eye E to be photographed due to, for example, flicks to thereby obtain movement positional information. The tracking unit 300 transmits a result of light reception obtained when the tracking starts to a controller 80 as reference information and then transmits a result of light reception obtained in each scan (light reception information) to the controller 80. The controller 80 compares the light reception information received from the tracking unit 300 to the reference information and calculates the movement positional information by a computing process to obtain the same light reception information as the reference information. The controller 80 drives the deflection unit 400 based on the calculated movement positional information. As a result of such a tracking control, the deflection unit 400 is driven so that any flicks of the examinee's eye E are balanced out. This largely reduces any motion of the fundus image displayed on a monitor 70. The dichroic mirror 91 transmits therethrough the light flux from the second photographing unit 200 but reflects the light flux from the tracking unit 300.

The first photographing optical system 100b is described below. The first photographing optical system 100b shares the optical path from the dichroic mirror 90 to the BS 71 described above with the first illumination optical system 100a. The first photographing optical system 100b includes a planar mirror 51, a PBS 52, a lens 53, a pinhole plate 54, a lens 55, and a photodetector 56. The photodetector 56 according to the embodiments is an APD (avalanche photodiode). The pinhole plate 54 is located at a position conjugate with the fundus.

The illumination light emitted from the light source 1 and reflected from the fundus travels backward the light travelling route described above referring to the first illumination optical system 100a. The reflected light is further reflected by the BS 71 and the planar mirror 51, and an S-polarized light alone transmits through the PBS 52. The transmitted light is focused on a pinhole of the pinhole plate 54 through the lens 53. The reflected light thus focused on the pinhole is received by the photodetector 56 through the lens 55. Though a part of the illumination light is reflected from a cornea, the pinhole plate 54 removes most of the light, thereby minimizing any adverse influences on a cornea-reflected image. Therefore, the photodetector 56 can receive the reflected light coming from the fundus while minimizing any adverse influences from the corneal reflection.

These optical devices constitute the first photographing optical system 100b. An image received and processed by the first photographing optical system 100b is the first fundus image. The first fundus image in one frame is obtained as a result of the main scan of the scan unit 15 and the sub scan of the galvano mirror for Y scan provided in the deflection unit 400. The angles of deflection (angles of oscillation) of the mirrors provided in the scan unit 15 and the deflection unit 400 are defined so that an angle of view of the fundus image obtained by the first photographing unit 100 stays at a given angle. To observe and photograph a given range of the fundus by a high magnifying power (for observation on a cellular level according to the embodiments), the angle of view is preferably set to about 1 to 5 degrees. The embodiments set the angle of view to 1.5 degrees. A photographing range of the first fundus image, though it depends on the visibility of the examinee's eye, is about 500 μm square.

When the reflection angles of the galvano mirror for X scan and the galvano mirror for Y scan provided in the deflection unit 400 are largely changed relative to the captured angle of view of the first fundus image, a position on the fundus where the first fundus image is captured is changed.

Next, the second photographing unit 200 is described. The second photographing unit is provided to capture a fundus image with a wider angle of view than that of the first photographing unit (second fundus image). The second fundus image is used as an image for position selection and position confirmation for obtaining the first fundus image with a narrower angle of view. The second photographing unit 200 provided to obtain such a second fundus image is preferably configured to obtain the fundus image of the examinee's eye E with a wide angle of view for the purpose of observation (for example, about 20 to 60 degrees) in real time. Specific examples of the second photographing unit 200 are, therefore, observation and photographing optical systems of fundus cameras presently available, optical and control systems of scanning laser ophthalmoscopes (SLO).

Next, the aberration detection optical system 110 is described. As described above, the aberration detection optical system 110 has a part of the optical devices on the optical path of the first illumination optical system 100a, thus sharing a part of the optical path with the first illumination optical system 100a. The aberration detection optical system 110 includes the light source 76, a lens 77, a PBS 78, a BS 75, a BS 71, a dichroic mirror 86, a PBS 85, a lens 84, a planar mirror 83, a lens 82, and the wavefront sensor 73. Further, the aberration detection optical system 110 shares the optical members from the BS 71 to the concave mirror 35 placed on the optical path of the first illumination optical system 100a.

The wavefront sensor 73 includes a microlens array having a large number of microlenses, and a two-dimensional imaging device 73a (two-dimensional photodetector) for receiving light fluxes transmitting through the microlens array. As the light source 76, which is an aberration detection light source (third light source), is preferably used a light source different to the light source 1 which emits light in infrared region. The light source 76 according to the embodiments is a laser diode which emits laser light having the wavelength of 780 nm.

The laser light emitted from the light source 76 is turned to collimated light flux by the lens 77 and polarized by the PBS 78 in a direction orthogonal to that of the illumination light from the light source 1 (P-polarized light). The resulting laser light is guided to the optical path of the first illumination optical system by the BS 75. The light emission end of the light source 76 is located at a position conjugate with the fundus. The PBS 78 redirects the light emitted from the light source 76 in a given direction of polarization, serving as a first polarizer provided in the wavefront compensation unit.

The laser light reflected by the BS 75 is converged on the fundus of the examinee's eye E through the optical path of the first illumination optical system 100a. The laser light reflected from the fundus is transmitted through the respective optical members of the first illumination optical system 100a and then reflected by the wavefront compensation device 72. The laser light is then departed from the optical path of the first illumination optical system 100a by the BS 71 and reflected by the dichroic mirror 86. The laser light is then guided to the wavefront sensor 73 through the PBS 85, lens 84, planar mirror 83, and lens 82.

The PBS 85 is a second polarizer provided in the wavefront compensation unit. The PBS 85 blocks a direction of polarization of the light emitted from the light source 76 and irradiated on the eye E (P-polarized light), while transmitting therethrough the light in a direction of polarization orthogonal to the direction of polarization (S-polarized light) to guide the transmitted light to the wavefront sensor 73. The dichroic mirror 86 transmits therethrough the light having the wavelength of the light source 1 (840 nm) and reflects the light having the wavelength of the aberration detection light source 76 (780 nm). Accordingly, of scattered lights of the laser light irradiated on the fundus, lights having the S-polarized light component are detected by the wavefront sensor 73. Thus, the wavefront sensor 73 is prevented from detecting any lights reflected by the optical devices or from the cornea.

The scan unit 15, reflection surface of the wavefront compensation device 72, and microlens array of the wavefront sensor 73 are all located at positions substantially conjugate with a pupil of the examinee's eye. The light reception surface of the wavefront sensor 73 is located at a position substantially conjugate with the fundus of the examinee's eye E. The wavefront sensor 73 is preferably a device configured to detect wavefront aberration including low-order and high-order aberrations. Specific examples of the wavefront sensor 73 thus configured are a Hartmann-Shack detector and a wavefront curvature sensor which detects a light intensity variation.

A preferable example of the wavefront compensation device 72 is a liquid crystal space light modulator wherein reflective LCOS (liquid crystal on silicon), for example, is used. The wavefront compensation device 72 is placed in the optical path of the fundus photographing optical system 100 to compensate the wavefront aberration of the examinee's eye by controlling the wavefront of the incident light. The wavefront compensation device 72 is located in a direction that enables aberration compensation for predetermined linearly polarized lights (S-polarized lights) such as the illumination light emitted from the light source 1 (S-polarized light), illumination light reflected from the fundus (S-polarized light), and reflected light of the wavefront aberration detection light (S-polarized light component). Thus provided, the wavefront compensation device 72 can modulate the S-polarized light components of the incident lights.

The wavefront compensation device 72 is located so that an arrangement direction of liquid crystal molecules in a liquid crystal layer is substantially in parallel with a plane of polarization of the incoming reflected light, and a predetermined plane where the liquid crystal molecules rotate in response to changing voltages applied to the liquid crystal layer is substantially in parallel with a plane including an incident optical axis and a reflective optical axis of the reflected light from the fundus entering the wavefront compensation device 72 and a normal of a mirror layer of the wavefront compensation device 72.

The wavefront compensation device 72 according to the embodiments is a liquid crystal modulating device wherein reflective LCOS (liquid crystal on silicon), for example, is used. However, the wavefront compensation device 72 is not necessarily limited thereto as far as a reflective wavefront compensation device is used. For example, a deformable mirror, which is an example of MEMS (micro electro mechanical systems), may be used. In place of the reflective wavefront compensation device, the wavefront compensation device 72 may be a transmission-type wavefront compensation device which compensates the wavefront aberration by transmitting therethrough the reflected light from the fundus.

In the description given so far, the aberration detection light source is the light source which emits the illumination light having the wavelength different to that of the first light source. However, the first light source may be used as the aberration detection light source.

According to the embodiments described so far, the wavefront sensor and the wavefront compensation device are located at positions conjugate with the pupil of the examinee's eye, however, may be located at a position substantially conjugate with any predetermined site in an anterior eye part of the examinee's eye, for example, a cornea.

Figure 3:
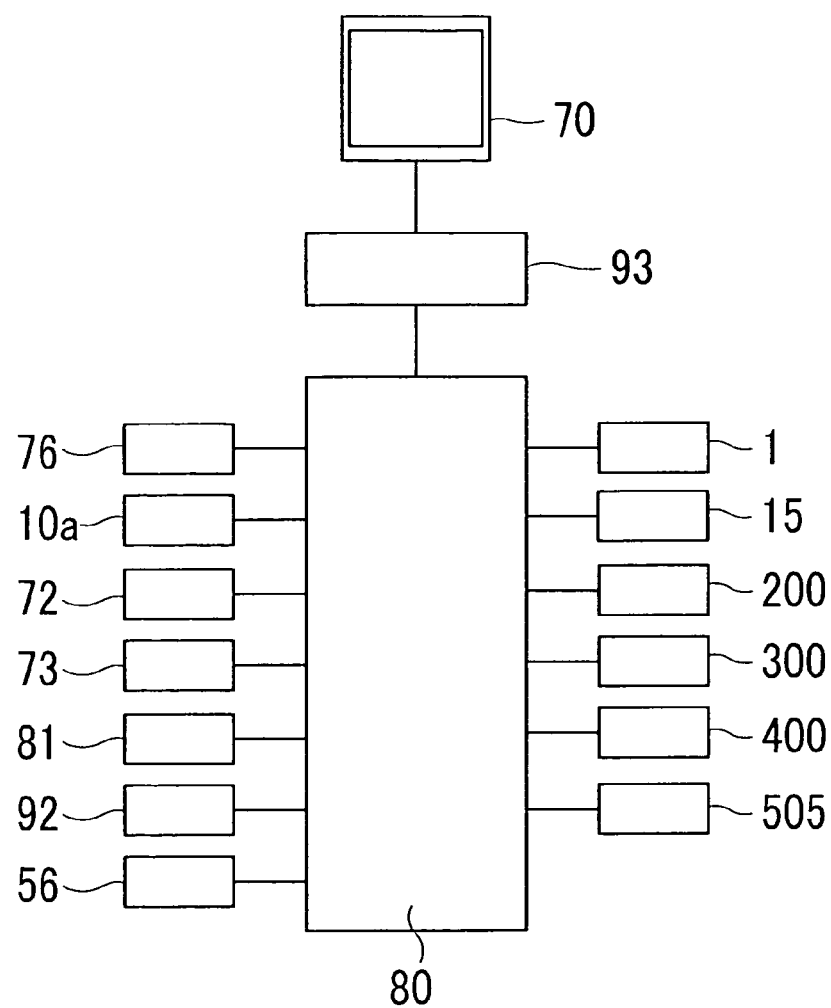
FIG. 3 is a block diagram to show a control system of the fundus photographing apparatus in the embodiment.

Next, a control system of the fundus photographing apparatus is described below. FIG. 3 is a block diagram illustrating the control system of the fundus photographing apparatus according to the embodiments. To the controller 80 in charge of controlling the whole apparatus are connected the light source 1, a drive mechanism 505, the scan unit 15, the photodetector 56, the wavefront compensation device 72, the wavefront sensor 73, the light source 76, the second photographing unit 200, the tracking unit 300, the deflection unit 400, and the drive unit 10a. Further, a storage unit 81, a control unit 92, an image processor 93, and the monitor 70 are connected to the controller 80.

The image processor 93 forms fundus images of the examinee's eye having different angles of view, which are the first and second fundus images, on the monitor 70 based on signals received by the photodetector 56 and the second photographing unit 200. The storage unit 81 stores therein various setting information (for example, a program for changing an effective region size described later) and captured images. An example of the monitor 70 is a monitor provided in an external personal computer or apparatus. The monitor 70 displays thereon the fundus images (first and second fundus images) updated by a given frame rate. The frame rate is, for example, 10 to 100 Hz. As a result, the fundus images are displayed as moving images. According to the embodiments, the controller 80 functions to serve as a display controller 80 of the monitor 70, a drive controller 80 of the deflection unit 400, and a light emission controller 80 of the light sources 1 and 76.

The wavefront compensation device 72 is controlled based on the wavefront aberration detected by the wavefront sensor 73, and the S-polarized light component of the reflected light of the light source 76 is removed as well as the illumination light emitted from the light source 1 and high-order aberration of the reflected illumination light. Thus, any aberration is removed from the illumination light emitted from the light source 1 and the reflected light thereof. As a result, the first fundus image having a high resolution from which the high-order aberration of the examinee's eye E has been removed (wavefront-compensated) is obtained. The low-order aberration is corrected by the visibility correction unit 10.

Figure 4:
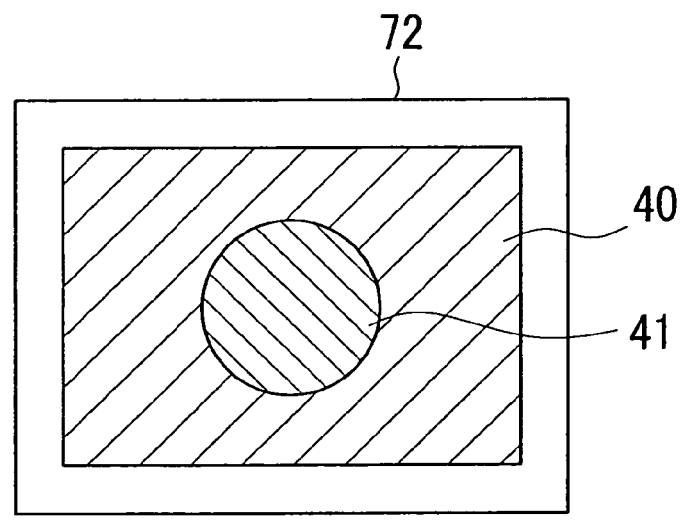
FIG. 4 is a diagram to explain a compensatable region and an effective region of a wavefront sensor.

FIG. 4 is a diagram to explain a compensatable region and an effective region of the wavefront sensor. A compensatable region 40 is a region of the wavefront compensation device 72 where the wavefront of an incident light is controllable. An effective region 41 is a region of the compensatable region 40 where aberration correction is enabled by a feedback control of the wavefront compensation device 72 based on a detection signal output from the wavefront sensor 73. According to the embodiments, the compensatable region 40 is in the size of 16 mm×12 mm, and the effective region 41 is in the size of φ8.64 mm. Because the compensatable region 40 is sizably larger than the effective region 41, any one of the position, size, and shape of the effective region 41 can be changed within the compensatable region 40 (described in detail later).

Figure 5A:
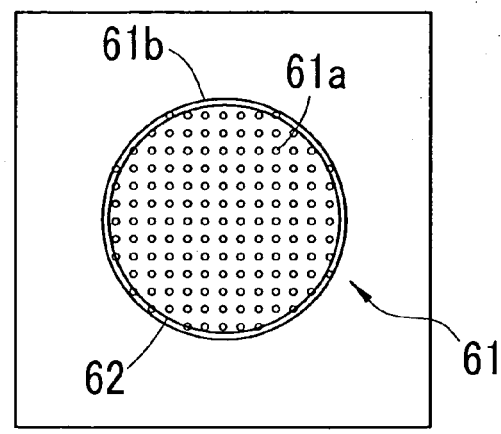
FIGS. 5A to 5C are diagrams to show specific examples of an index pattern image and the effective region on the compensatable region of the wavefront sensor.
Figure 5B:
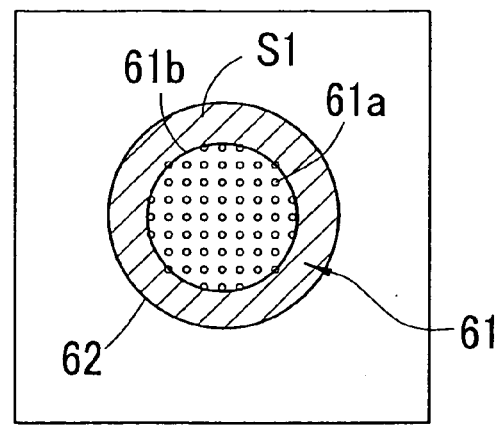
Figure 5C:
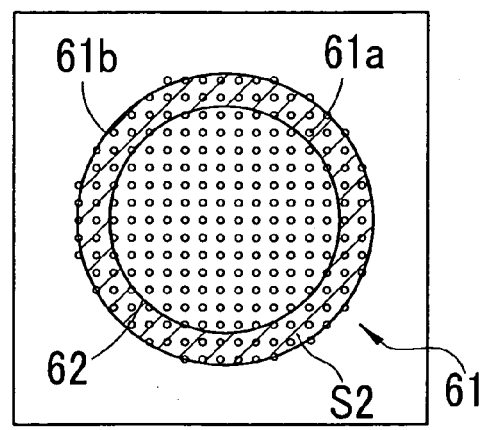
Figure 6A:
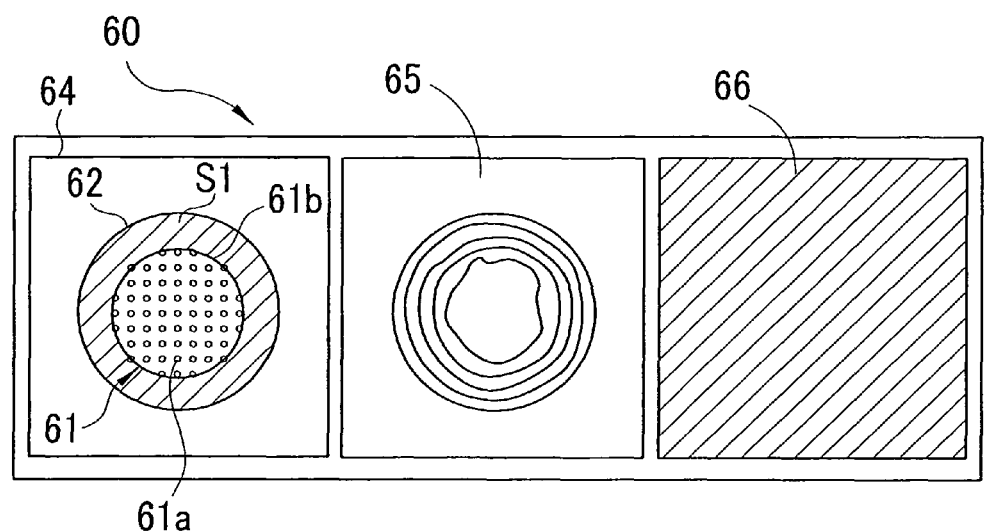
FIGS. 6A and 6B are diagrams to show an aberration correcting screen displayed on a screen of a monitor.
Figure 6B:
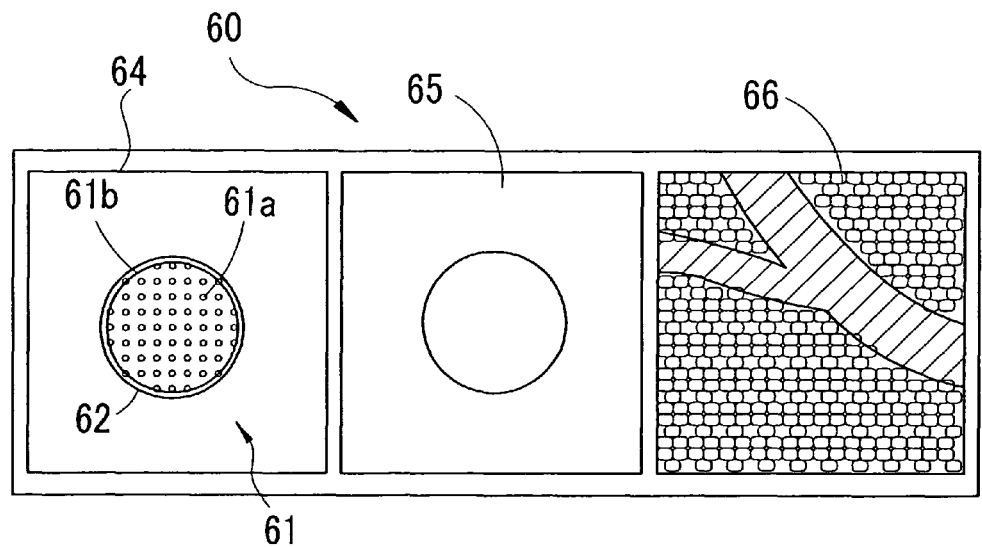

FIGS. 5A to 5C are diagrams to show specific examples of the index pattern image and the effective region on the compensatable region of the wavefront sensor. FIGS. 6A and 6B are diagrams to show an aberration correcting screen 60 displayed on the monitor 70. The aberration correcting screen 60 displays thereon the index pattern image 61 received by the two-dimensional imaging device 73a of the wavefront sensor 73 (Hartmann image according to the embodiments, hereinafter referred to as a Hartmann image), an aberration correction graphic 65 graphically displaying a degree of aberration correction (remaining aberration), and a cell image 66 of the fundus actually photographed.

The Hartmann image (dot pattern image) 61 represents a plurality of assembled point images 61a received on the wavefront sensor 73. The fundus reflected light passing through the lens array is received by the two-dimensional imaging device 73a of the wavefront sensor 73 and captured as a Hartmann image. The Hartmann image 61 is displayed on the monitor 70. A region where the point images 61a are detected by the wavefront sensor 73 is an aberration detectable region.

A circle 62 is a virtual illustration of the effective region where the aberration correction is effective (enabled) by controlling the wavefront of the wavefront compensation device 72 on the two-dimensional imaging device 73a. A graphic representing the circle 62 is superimposed on the Hartmann image and displayed on the monitor 70. A mark positioned at the center of the circle 62 is a graphic illustrating a center position of the effective region on the wavefront sensor 73.

In the storage unit 81 are previously stored an outer periphery, a region, and positional information of the circle 62 on the wavefront sensor 73. These data are preferably calculated by calibration or simulation beforehand. Of all of incident lights entering the wavefront compensation device 72, the effective region can only receive light fluxes limited to a partial area (for example, an area having the diameter of 6 mm on a pupil). Any other incident lights are reflected in the direction of the photodetector 54 with their wavefronts uncompensated.

The aberration correction is performed based on a result of aberration detection obtained by the wavefront sensor 73. Therefore, the aberration detection needs to be accurate to accurately perform the aberration correction. Hereinafter is described a relationship between the Hartmann image and the effective region for aberration detection.

Supposing that a region where the Hartmann image 61 is formed (Hartmann image outer periphery 61b) has a size substantially equal to the region formed by the circle 62 (effective region) during the aberration detection, the wavefront condition is correctly detectable, therefore, the aberration correction can be optimally performed (see FIG. 5A).

In the case where the region where the Hartmann image 61 is formed has a size smaller than the region formed by the circle 62 (effective region), there is a region S1 where the Hartmann image 61 is not formed in the effective region. In the region formed by the circle 62, therefore, the wavefront condition is not detectable in region S1 where the Hartmann image 61 is not formed. In the event that the wavefront data is thus partly missing, it is not possible to obtain the whole wavefront information, failing to correctly measure the wavefront aberration in the wavefront correction region (see FIG. 5B). Referring to FIG. 6A, even after the aberration correction is performed, the aberration is not properly removed as illustrated in the aberration correction graphic 65 and it becomes difficult to obtain a suitable image as illustrated in the cell image 66.

In the case where the region where the Hartmann image 61 is formed has a size larger than the region formed by the circle 62 (effective region), reflected light flux can be received in a region S2 where the region where the Hartmann image 61 is formed is larger than the region formed by the circle 62, however, the wavefront compensation by the wavefront compensation device 72 is not possible (see FIG. 5C). Because the information of aberration in the region S2, though successfully detected, cannot be reflected on (fails to contribute to) the wavefront compensation device 72, it becomes difficult to obtain an image having a high resolving power.

As is clear from the description given so far, it is desirable that the Hartmann image and the effective region be substantially equal in size in order to properly perform the aberration detection. According to the embodiments, information of the pupil of the examinee's eye is obtained, and the wavefront compensation device 72 is controlled depending on the obtained pupil information to resize the effective region that enables the aberration correction control. For example, the effective region is upsized or downsized depending on the size of the Hartmann image. Then, the region formed by the circle 62 is equal in size to the Hartmann image 61 as illustrated in FIG. 5A, enabling the aberration to be correctly detected and corrected (described in detail later). Referring to FIG. 6B, the aberration removal succeeds as illustrated in an aberration correction graphic 65, and an image having a high resolving power where the aberration has been removed can be displayed as the cell image 66.

Figure 7:
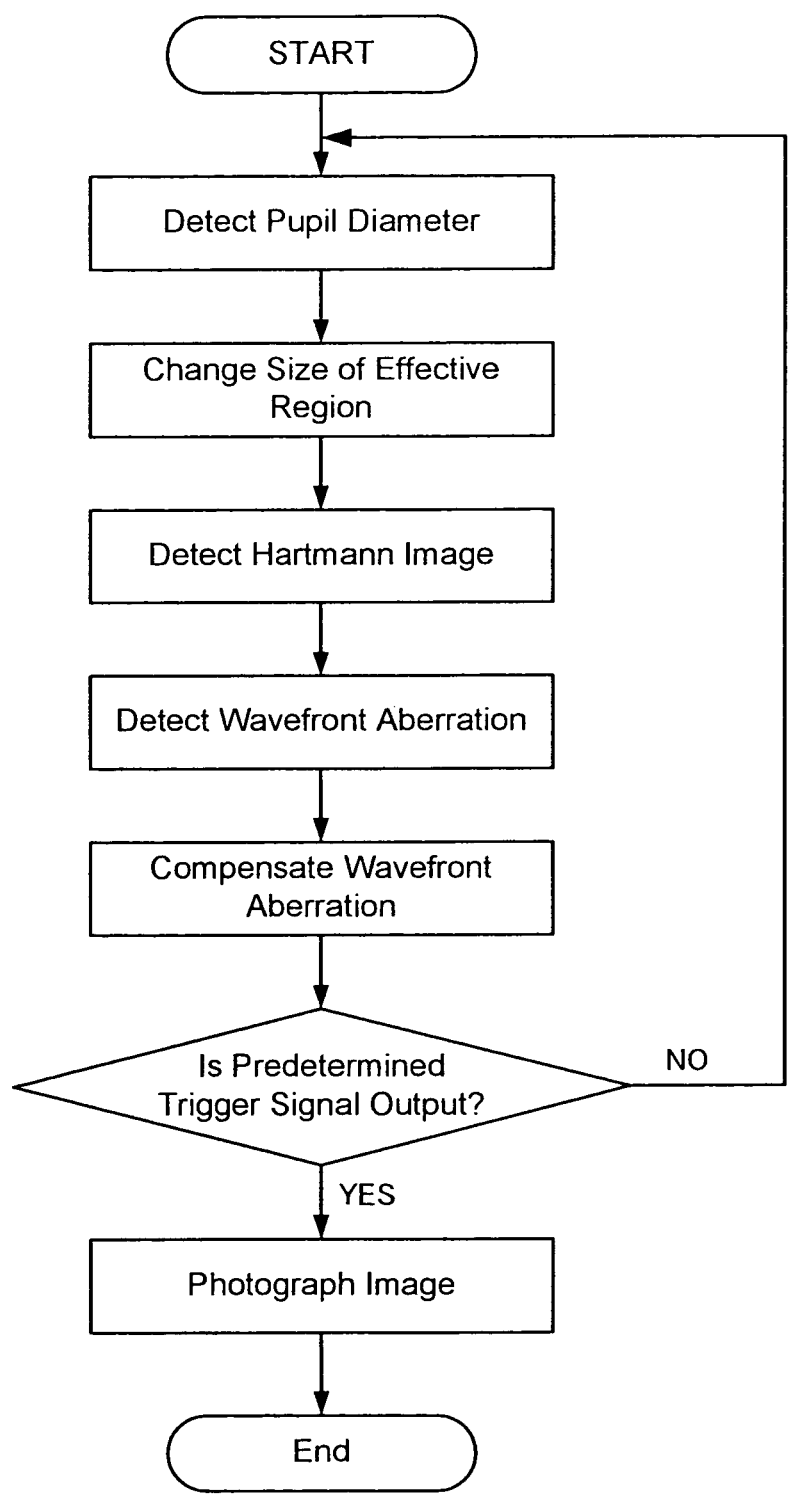
FIG. 7 is a flowchart to explain operations in a first embodiment.

A first embodiment of the fundus photographing apparatus thus characterized is hereinafter described. According to the first embodiment, the effective region is resized (corrected) depending on the Hartmann image size. Referring to a flowchart illustrated in FIG. 7, a description is given to a control operation performed to obtain a favorable fundus image where wavefront aberration has been corrected.

An examiner, while observing an image displayed on the screen of the monitor 70, performs rough alignment by positionally adjusting the jaw rest 610 manually or automatically. The examiner further instructs an examinee to watch a fixation target not illustrated in the drawings. When a measurement switch not illustrated in the drawings is pressed by the examiner after the rough alignment of the jaw rest 610 is done, the controller 80 causes the visibility correction unit 10 to perform visibility correction.

Then, the controller 80 detects information of the pupil of the examinee's eye (for example, pupil diameter) based on a light reception signal output from a light receiver which receives the reflected light from the examinee's eye. The controller 80 controls the wavefront compensation device 72 based on the detected pupil information, thereby resizing the effective region where the aberration correction control is effective. For example, the controller 80 resizes the effective region based on the detection result of the wavefront sensor 73.

A first example of the resizing operation is described. The controller 80 detects an outer edge portion of a light reception region of the index pattern image by the wavefront sensor 73 and resizes the effective region based on a size of the detected outer edge portion. More specifically, the controller 80 sequentially detects positions of the point images received on an outermost side of the Hartmann image 61 received by the wavefront sensor 73 to finally detect positional information of the Hartmann image outer periphery 61b. Then, the controller 80 compares the Hartmann image outer periphery 61b to the circle 62. In the case where a differential region between the region formed by the circle 62 and the region formed by the Hartmann image outer periphery 61b exceeds a given threshold value, for example, the controller 80 resizes the effective region 41 of the wavefront compensation device 72.

A second example of the resizing operation is described. The controller 80 calculates a center position of the light reception region of the index pattern image from the detected outer edge portion and detect a dimension from a central coordinate of the center position to the outer edge portion to resize the effective region 41 based on the detected dimension from the central coordinate to the outer edge portion. More specifically, the controller 80 detects a position of the central coordinate of the Hartmann image 61 and calculates distances from the central coordinate to the Hartmann image outer periphery 61b in radial directions. Then, the controller 80 detects a minimal value of the calculated distances and resizes the effective region 41 of the wavefront compensation device 72 based on the minimal value so that the minimal distance value and the radius of the circle 62 are equal or substantially equal to each other.

An index region used for aberration detection is resized in the Hartmann image received by the wavefront sensor 73 so as to match the resized effective region 41. According to the present embodiment, an initial effective region before the pupil diameter is detected is in the size of φ4.0 mm. The initial effective region may be provided in different sizes, and the size of the initial effective region may be arbitrarily set by the examiner.

An operation for changing the effective region is described below. The storage unit 81 stores therein a pupil diameter-effective region correlation table. In the table are set effective regions in optimal sizes for different pupil diameters. For example, the effective region on pupil is in the size of φ5.0 mm for the pupil diameter of φ5.0 mm. The controller 80 obtains the effective region suitable for the detected pupil diameter from the storage unit 81 and accordingly changes the initial effective region to the obtained effective region. To create the pupil diameter-effective region correlation table, the Hartmann image for a given pupil diameter, for example, is detected beforehand by the apparatus, and the effective region equal or substantially equal in size to the detected Hartmann image is obtained. The effective region is thus calculated for each of eye models respectively having different pupil diameters and tabulated in the pupil diameter-effective region correlation table. As described above, the effective region is changed based on the pupil diameter.

In place of changing the effective region based on the pupil diameter-effective region correlation table stored in the storage unit 81 as described in the present embodiment, the effective region may be calculated by a given operational expression based on the detected pupil diameter to change the effective region to the calculated effective region.

Next, the controller 80 detects any displacement of a position of gravity between the effective region (for example, circle 62) of the wavefront compensation device 72 set on the wavefront sensor 73 and the light reception region (wavefront measurement region) of the index pattern image (for example, Hartmann image 61) received by the wavefront sensor 73. The controller 80 positionally adjusts the jaw rest 610 manually or automatically. In the case where the photographing unit 500 is configured to be movable relative to the eye E, the controller 80 may move the photographing unit 500 so that the displacement information stays in a range of tolerance. A light deflector which changes an advancing direction of measured light flux may be provided in the optical path of the detection optical system 110 and driven to optically adjust the positional relationship. These steps are suggested to correct any displacement generated between the circle 62 and the Hartmann image 61 whenever the eye E and the photographing unit 500 are misaligned relative to each other.

The controller 80 determines whether the region formed by the circle 62 is staying in the region formed by the Hartmann image outer periphery 61b. In the case where the region formed by the circle 62 fails to stay within the region formed by the Hartmann image outer periphery 61b, the controller 80 adjusts relative positions of the eye E and the photographing unit 500. While the region formed by the circle 62 is staying in the region formed by the Hartmann image outer periphery 61b, the controller 80 detects the wavefront aberration of the examinee's eye E based on the detection result of the wavefront sensor 73 and starts to photograph the fundus using the fundus photographing optical system 100.

The controller 80 calculates an amount of aberration compensation based on the obtained aberration detection result and controls an amount of aberration correction in the effective region 41 of the wavefront compensation device 72 based on the calculated compensation amount to compensate the wavefront aberration.

Then, the controller 80 detects the pupil diameter from an image of the anterior eye part to resize the effective region 41. The controller 80 then newly obtains the Hartmann image output from the wavefront sensor 73 to detect wavefront aberration of the obtained image. Then, the controller 80 calculates the amount of aberration compensation based on the detected wavefront aberration, and then controls the amount of aberration correction in the effective region 41 of the wavefront compensation device 72 based on the calculation result to compensate the wavefront aberration.

The controller 80 performs a second feedback control which repeatedly detects the wavefront aberration of the examinee's eye based on the detection signal output from the wavefront sensor 73 and controls the wavefront compensation device 72 based on the obtained detection result. During the wavefront aberration compensation, the second feedback control is reflected on a fundus moving image obtained at the same time. The second feedback control thus compensates the wavefront of the fundus reflected light, thereby reducing blur of the fundus moving image. Even if the aberration condition of the examinee's eye relative to the fundus photographing apparatus changes as the pupil diameter of the examinee's eye changes, a clear fundus image is successfully obtained.

The second feedback control continues until the photographing operation ends. When a predetermined trigger signal is output while the fundus moving image is being obtained by the second feedback control, a fundus cell image thus obtained is stored in the storage unit 81 as a moving image or a still image.

Because of a possibility that the pupil diameter of the eye E changes during the second feedback control, the controller 80 may further perform a first feedback control which repeatedly obtains the pupil information of the examinee's eye and resizes the effective region 41 in response to any changes on the obtained pupil information.

When the effective region 41 of the wavefront compensation device 72 is resized depending on the pupil diameter, the aberration correction can always obtain a favorable result for different pupil diameters of different examinees' eyes. As a result, a favorable fundus image having a high resolving power can be obtained irrespective of individual differences of examinees' eyes.

Figure 8:
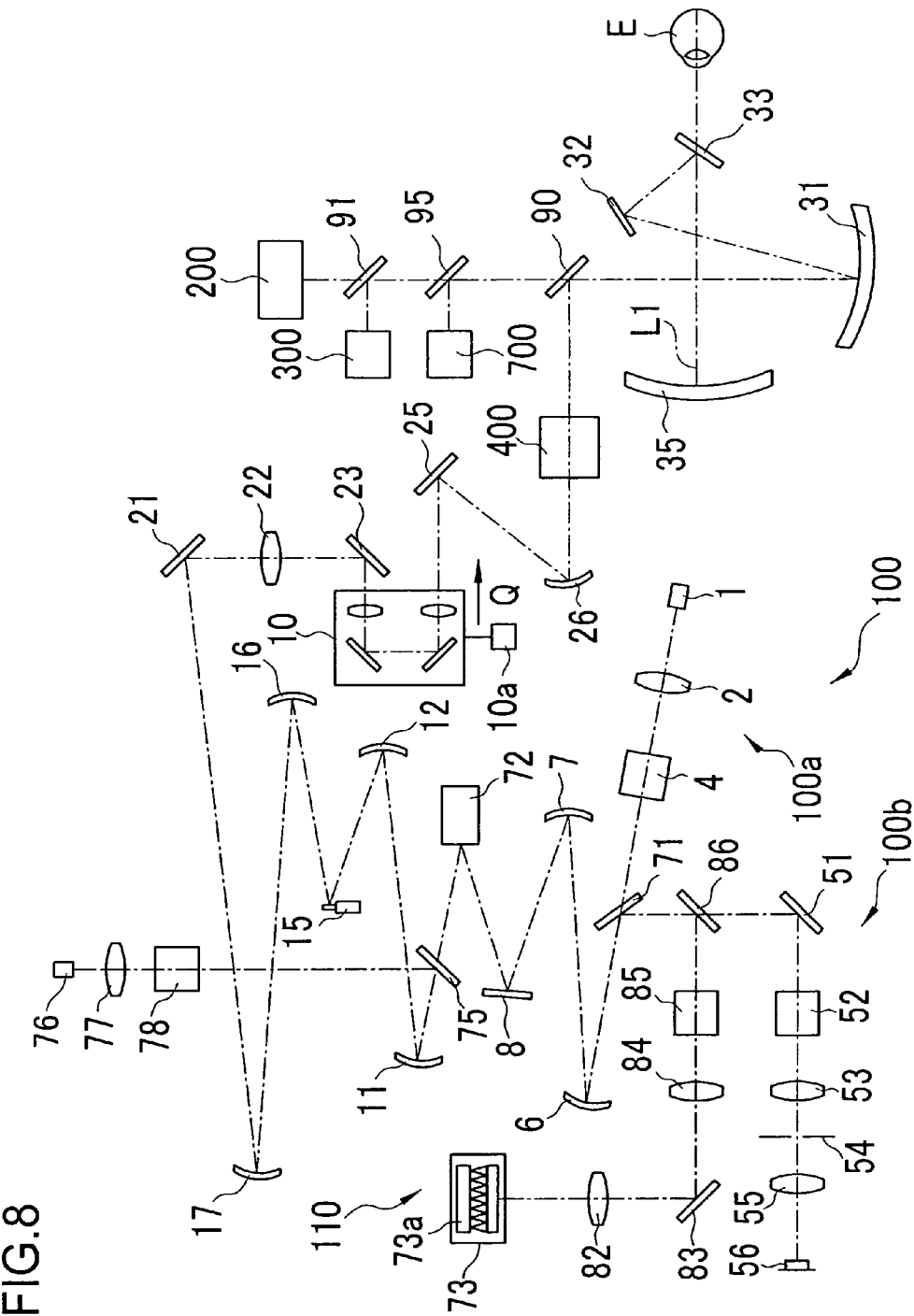
FIG. 8 is a schematic view to show an optical system of a fundus photographing apparatus including an anterior eye part observation system.

Below is described a pupil diameter detection method by the fundus photographing apparatus provided with an anterior eye part observation unit 700 as a part of the optical system as illustrated in FIG. 8.

In the optical system, the anterior eye part observation unit 700 irradiates a visible light on an anterior eye part of the examinee's eye to capture a front image of the anterior eye part. A dichroic mirror 95 transmits therethrough the light fluxes from the second photographing unit 200 and the tracking unit 300 and reflects the light flux from the anterior eye part observation unit 700.

Figure 9:
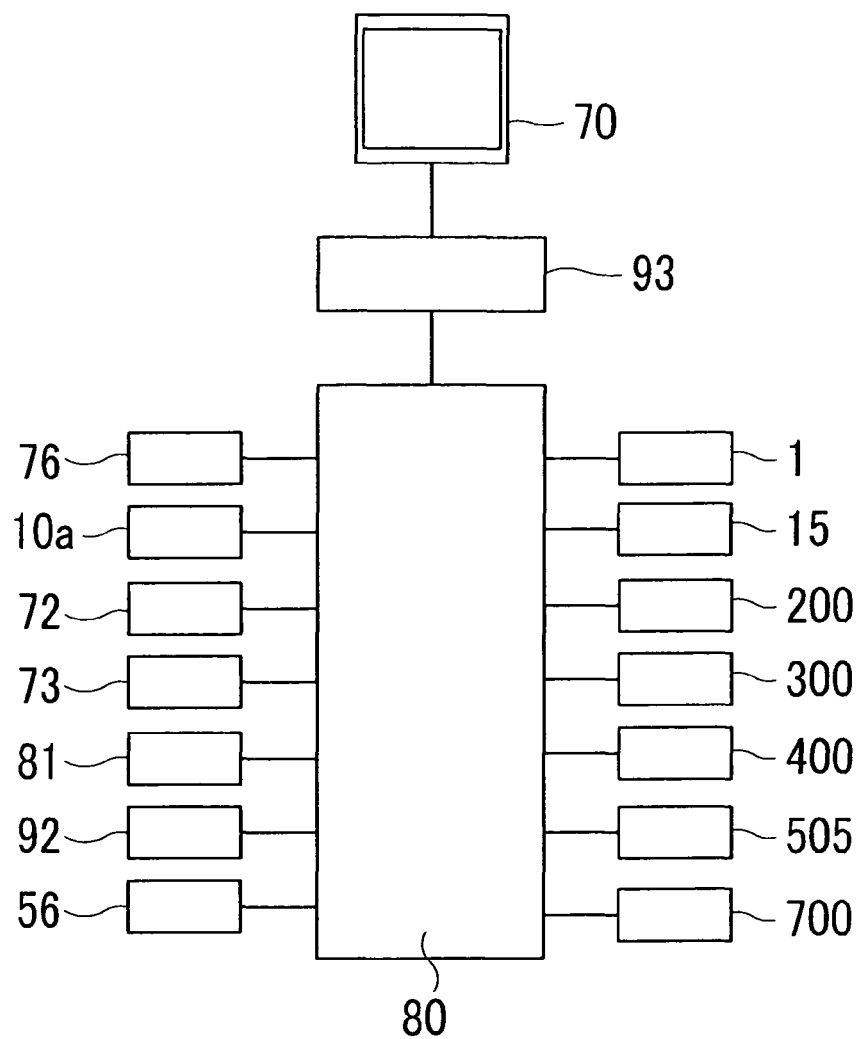
FIG. 9 is a block diagram showing a control system of the fundus photographing apparatus including the anterior eye part observation system.

As illustrated in FIG. 9, the anterior eye part observation unit 700 is connected to the controller 80 in charge of controlling the whole apparatus.

The controller 80 causes the anterior eye part observation unit 700 to receive the reflected light from the examinee's eye to detect the pupil diameter from the anterior eye part image thus obtained. A method for detecting the pupil diameter by obtaining an edge position of the pupil from the anterior eye part image is described referring to FIGS. 10A to 10C.

Figure 10A:
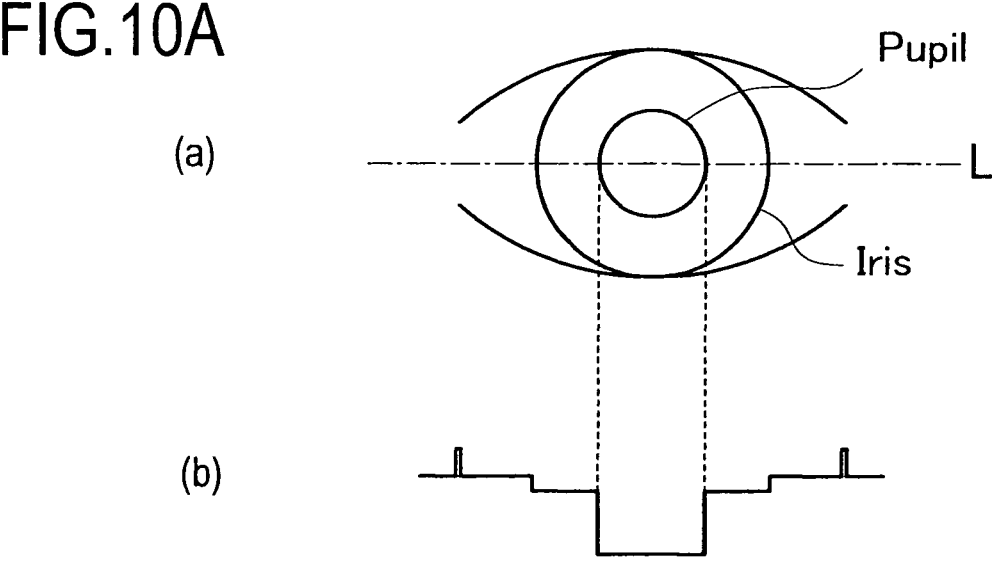
FIGS. 10A to 10C are diagrams to explain a method for detecting a pupil diameter with the fundus photographing apparatus including the anterior eye part observation system.
Figure 10B:
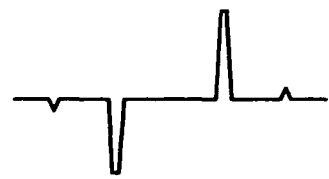
Figure 10C:
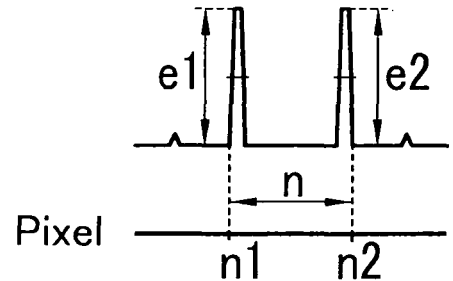

In FIG. 10A, (a) is an illustration of a captured anterior eye part image, and (b) is an illustration of an image signal on a scan line L. To define a boundary (edge) between a pupil (a dark part) and an iris (a bright part), a signal waveform illustrated in FIG. 10A (b) is subjected to a differentiation process. The differentiated signal waveform is illustrated in FIG. 10B. Because the signal then is a positive/negative signal, the signal, when squared, results in a positive value signal illustrated in FIG. 10C. Supposing in the illustration of FIG. 10C that an edge between an initial waveform signal having a height e1 and a last waveform signal having a height e2 is defined as a point of ½ of each height (amplitude), pixel positions n1 and n2 are coordinate positions of the edge on the scan line L.

Further, the number of pixels n between the pixel positions n1 and n2 is obtained. A distance between the pixel positions n1 and n2 (pupil diameter PS') is obtained from the formula:

$$PS'=n*K/P$$

where the length of a pixel is K and an optical magnifying power is P. The values of K and P are known values specific to the apparatus, therefore, the pupil diameter is calculated when the number of pixels n is obtained.

A center position of the pupil is detected based on contour information of the pupil, and the pupil diameters measured from the center position in radial directions are calculated. When the anterior eye part observation unit 700 is used to detect the pupil diameter, the pupil diameter is more accurately calculated. The effective region 41 is accordingly more suitably resized, and the aberration correction obtains an even more favorable result.

The present embodiment is applicable to an examinee's eye where a pupil (Hartmann image) has an irregular shape. For example, the examinee's eye may have such pupil that includes a waveform shape or has an elliptical shape, in which case an inscribed circle including the irregular pupil region on an inner side thereof may be changed as the effective region.

In the case where the examinee's eye has such pupil that includes a waveform shape or has an elliptical shape, a circumscribed circle including the irregular pupil region may be changed as the effective region. In the case of using the circumscribe circle as the effective region, however, it is necessary to detect the aberration based on the assumption that the irregular pupil region has a circular shape because of a region where the aberration is undetectable generated between the circumscribed circle and the pupil region.

According to the present embodiment, the pupil diameter is detected whenever necessary by the first feedback control to resize the effective region 41 of the wavefront compensation device 72. Instead, the size of the effective region 41 may be left unchanged as long as the pupil diameter variation (for example, φ±0.3 mm) is staying in a given range of tolerance, or the effective region 41 may be resized only when the photographing operation starts.

The present embodiment changes the radius of the circular effective region. This is, however, unnecessary as far as the effective region is resized based on the pupil information. The effective region may have an elliptical shape, a triangular shape, or a rectangular shape, in which any of these shapes is resized. The controller 80 may detect the outer peripheral portion of the Hartmann image to resize the effective region 41 of the wavefront compensation device 72 so that the outer edge shape of the Hartmann image is consistent with the size of the effective region 41. The shape of the effective region may be arbitrarily set by the examiner.

Though the sensor which detects the pupil information is provided in the embodiment described so far, the effective region may be resized depending on pupil information obtained by a pupil diameter measuring device separately provided.

To resize the effective region, it is unnecessary that the size of the effective region 41 exactly match the pupil size of the examinee's eye as long as a favorable aberration correction result is obtained. For example, the effective region 41 may be resized stepwise (for example, per 1 mm in a range of φ=3.0 mm to 8.0 mm,) to selectively set the size of the effective region 41 as close to the detected pupil size as possible.

According to the embodiment described so far, the index region used for aberration detection is resized depending on any changes of the effective region 41. Instead, the controller 80 may resize the index region used for aberration detection in the Hartmann image received by the wavefront sensor 73 depending on the obtained pupil information of the eye E or may detect the Hartmann image outer periphery 61b to measure the wavefront aberration based on the whole index pattern image received by the wavefront sensor 73.

Figure 11A:
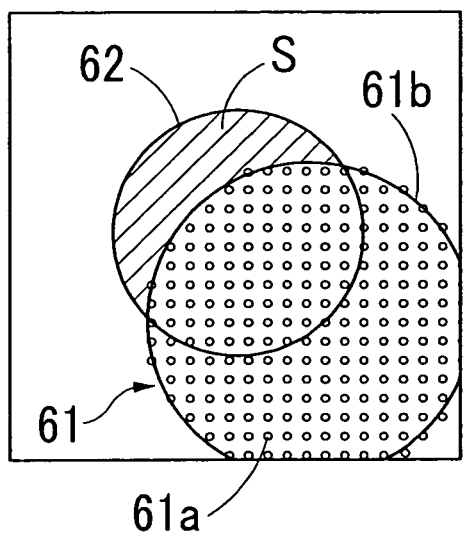
FIGS. 11A and 11B are diagrams to explain specific examples of the index pattern image and the effective region on the compensatable region of the wavefront sensor.
Figure 11B:
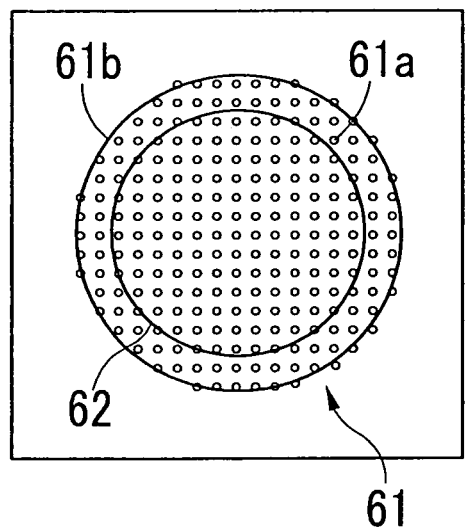
Figure 12A:
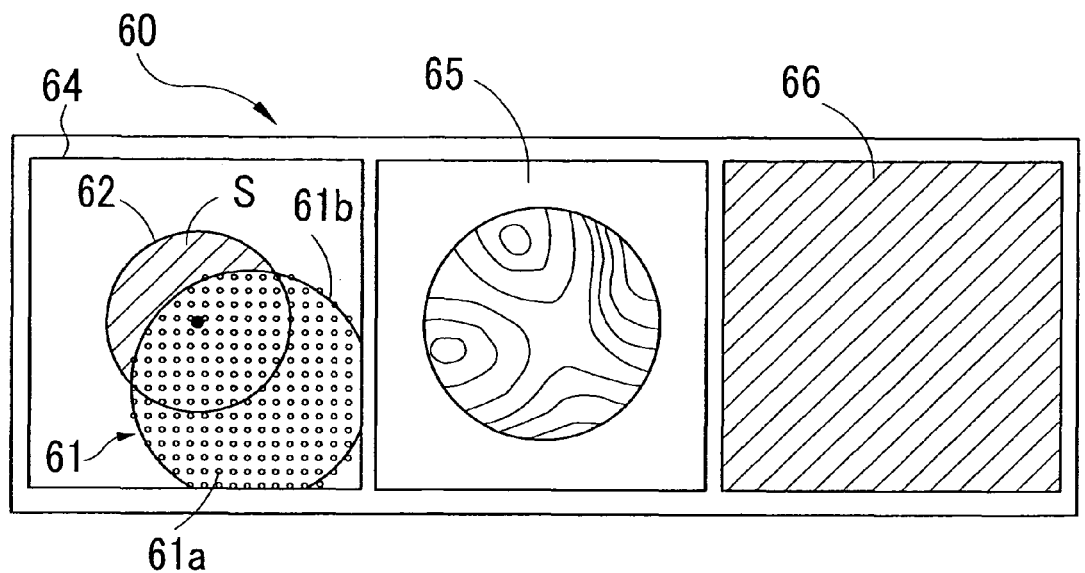
FIGS. 12A and 12B are diagrams to show an aberration correction screen displayed on the screen of the monitor.

Next, a second embodiment of the fundus photographing apparatus is hereinafter described. As described so far, the aberration correction is performed based on the aberration detection result obtained by the wavefront sensor 73, meaning that the wavefront condition is detectable in a region of region formed by the circle 62 where the Hartmann image 61 is formed (see FIG. 11B). On the other hand, the wavefront condition is undetectable in a region S of the region formed by the circle 62 where the Hartmann image 61 is not formed. In the event that the wavefront data is thus partly missing, it is not possible to obtain the whole wavefront information, failing to correctly measure the wavefront aberration in the wavefront correction region (see FIG. 11A). Referring to FIG. 12A, even after the aberration correction is performed, the aberration is not properly removed as illustrated in an aberration correction graphic 65 and it becomes difficult to obtain a suitable image as illustrated in a cell image 66.

Figure 13:
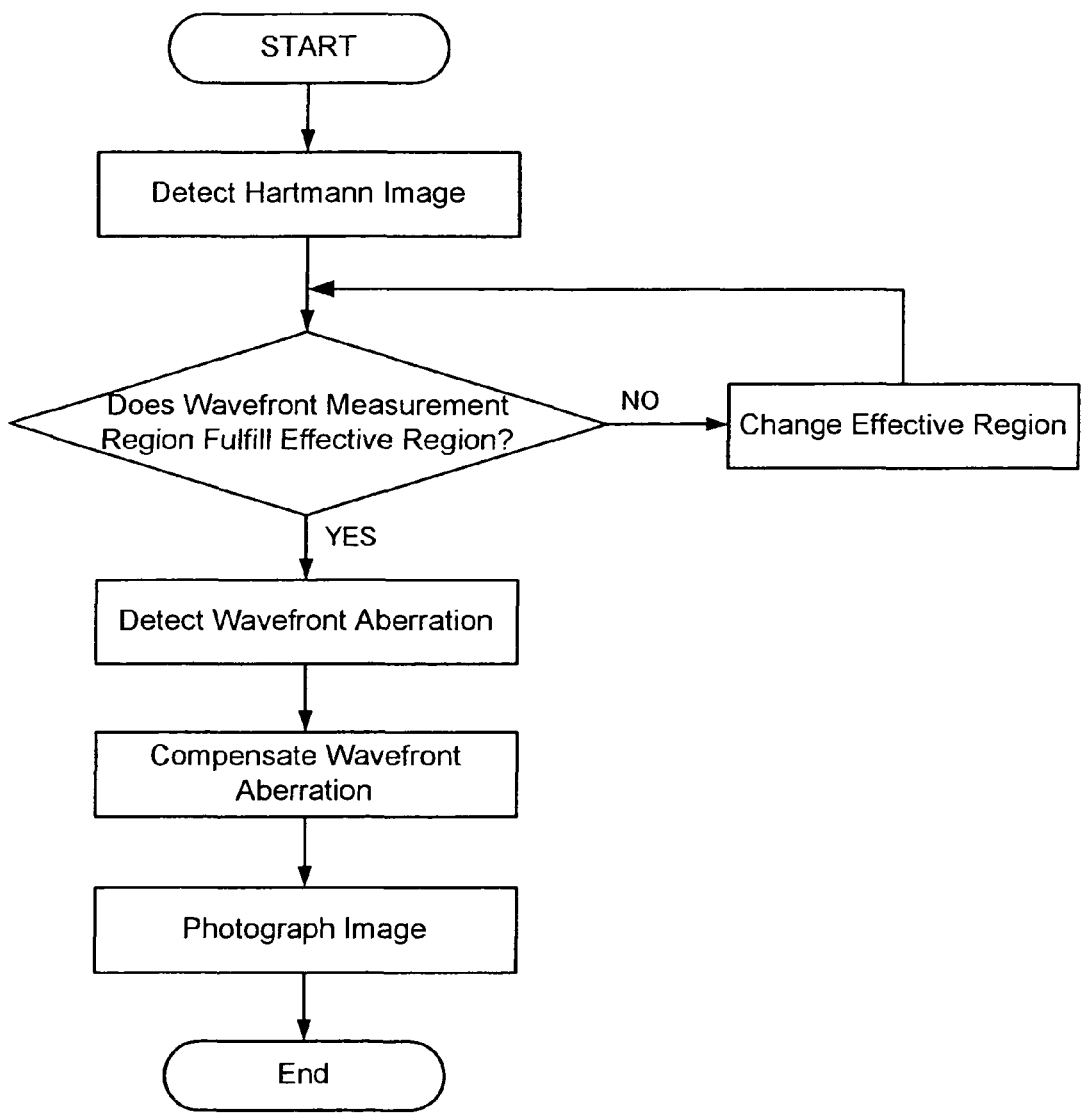
FIG. 13 is a flowchart to explain operations in a second embodiment.

The second embodiment, therefore, corrects any positional displacement between the wavefront measurement region and the effective region of the wavefront compensation device 72. An operation of the positional displacement correction is described referring to a flowchart illustrated in FIG. 13.

An examiner, while observing an anterior eye part image, which is not illustrated in the drawings, displayed on the screen of the monitor 70, performs rough alignment by positionally adjusting the jaw rest 610 manually or automatically. The examiner further instructs an examinee to watch a fixation target not illustrated in the drawings.

When a measurement switch not illustrated in the drawings is pressed by the examiner after the rough alignment of the jaw rest 610 is done, the controller 80 causes the visibility correction unit 10 to perform visibility correction, which is followed by wavefront detection necessary for aberration correction.

Next, the controller 80 detects information of the positional displacement between the effective region of the wavefront compensation device 72 set on the wavefront sensor 73 (for example, circle 62) and the light reception region (wavefront measurement region) of the index pattern image obtained by the wavefront sensor 73 (for example, Hartmann image 61).

The controller 80 positionally adjusts the jaw rest 610 manually or automatically. In the case where the photographing unit 500 is configured to be movable relative to the eye E, the controller 80 may move the photographing unit 500 so that the displacement information stays in a range of tolerance.

The controller 80 determines whether the region formed by the circle 62 is staying in the region formed by the Hartmann image outer periphery 61b. In the case where the region formed by the circle 62 fails to stay within the region formed by the Hartmann image outer periphery 61b, the controller 80 adjusts relative positions of the eye E and the photographing unit 500. While the region formed by the circle 62 is staying in the region formed by the Hartmann image outer periphery 61b, the controller 80 detects the wavefront aberration of the examinee's eye E based on the detection result obtained by the wavefront sensor 73 and starts to photograph the fundus using the fundus photographing optical system 100.

The controller 80 calculates an amount of aberration compensation based on the obtained detection result and controls the effective region 41 of the wavefront compensation device 72 based on the calculated compensation amount to compensate the wavefront aberration. The controller 80 then newly obtains the Hartmann image output from the wavefront sensor 73 to detect wavefront aberration of the obtained image. Then, the controller 80 calculates the amount of aberration compensation based on the aberration detection result and controls the effective region 41 of the wavefront compensation device 72 based on the calculation result to compensate the wavefront aberration. Thus, the controller 80 performs a feedback control which repeatedly performs the aberration detection and wavefront compensation control based on the aberration detection result.

In the case of LCOS, a phase pattern for compensation is feedback-controlled in a loop process including; detection of the wavefront aberration by the wavefront sensor 73, calculation of the phase pattern of LCOS based on an obtained aberration detection result, and voltage application to pixels of LCOS based on an obtained calculation result. Then, an index of refraction of a liquid crystal layer of LCOS is changed whenever necessary based on the detected wavefront aberration to correct any wavefront distortion of the fundus reflected light.

In the case of a deformable mirror, an overall shape of the mirror is feedback-controlled in a loop process including; detection of the wavefront aberration by the wavefront sensor 73, calculation of the mirror shape based on an obtained aberration detection result, and voltage application to drive units of the deformable mirror based on an obtained calculation result. Then, the overall shape of the mirror is changed whenever necessary based on the detected wavefront aberration to correct any wavefront distortion of the fundus reflected light.

During the wavefront aberration compensation, the feedback control is reflected on a fundus moving image obtained at the same time. The feedback control thus compensates the wavefront of the fundus reflected light, thereby reducing blur of the fundus moving image. Even if the current aberration of the examinee's eye changes relative to the fundus photographing apparatus as the fixation condition or the position of the examinee's eye changes, a clear fundus image is successfully obtained.

The feedback control continues until the photographing operation ends. When a predetermined trigger signal is output while the fundus moving image is being obtained by the feedback control, a fundus cell image thus obtained is stored in the storage unit 81 as a moving image or a still image.

After the examinee's eye and the apparatus are positionally aligned relative to each other, it is still possible that the examinee's eye E and the apparatus are positionally displaced from each other in the case where, for example, the fixation of the examinee's eye E fails. In that case, the wavefront measurement region where the wavefront is actually measured (region formed by the Hartmann image outer periphery 61b) is displaced from a region necessary for controlling the effective region 41 of the wavefront compensation device 72 (region formed by the circle 62). As a result, there is not enough wavefront information that needs to be obtained to control the effective region 41 (region formed by the circle 62).

In the event of any positional displacement between the wavefront measurement region and the effective region of the wavefront compensation device, the controller 80 controls the wavefront compensation device 72 so as to correct a positional displacement in a direction orthogonal to an optical axis between the effective region 41 of the wavefront compensation device 72 where the aberration correction control is effective and the wavefront measurement region where the wavefront aberration is measured by the aberration measurement optical system 110. For example, the controller 80 detects information of the positional displacement in the direction orthogonal to the optical axis between the effective region 41 and the wavefront measurement region. In the case where the detected displacement information is beyond a range of tolerance, the controller 80 positionally adjusts the effective region 41 so that the displacement information falls within the range of tolerance.

A more detailed description is given below. First, the controller 80 sequentially detects positions of point images received on an outermost side of the Hartmann image 61 received by the wavefront sensor 73 to detect positional information of the Hartmann image outer periphery 61b. As a result, a detection region of the Hartmann image 61 (wavefront measurement region) is obtained.

Then, the controller 80 compares the positional information of the Hartmann image outer periphery 61b to the positional information of the circle 62 (effective region) and determines whether the wavefront measurement region fulfills the effective region based on a comparison result thereby obtained. As a result, it is determined whether the aberration of the eye E is correctable.

More specifically, the controller 80 compares the region encompassed with the Hartmann image outer periphery 61b (see dotted line) to the region encompassed with the circle 62. The controller 80 determines the comparison result as acceptable (OK) when the region formed by the circle 62 is staying in the region formed by the Hartmann image outer periphery 61b (see FIG. 11B). On the other hand, the controller 80 determines the comparison result as unacceptable (NG) in the case where the region formed by the circle 62 fails to stay within the region formed by the Hartmann image outer periphery 61b (see FIG. 11A).

With the NG result, the controller 80 controls the wavefront compensation device 72 so that the region formed by the circle 62 is included in the region formed by the outer periphery 61b of the Hartmann image 61 to change the effective region 41 within the compensatable region 40 of the wavefront compensation device 72. Because the wavefront of the incident light is controllable (for example, movable or enlargeable) in the compensatable region 40, the effective region 41 becomes changeable (resettable) within the compensatable region 64 by changing a position at which the wavefront of the incident light is controlled.

Figure 12B:
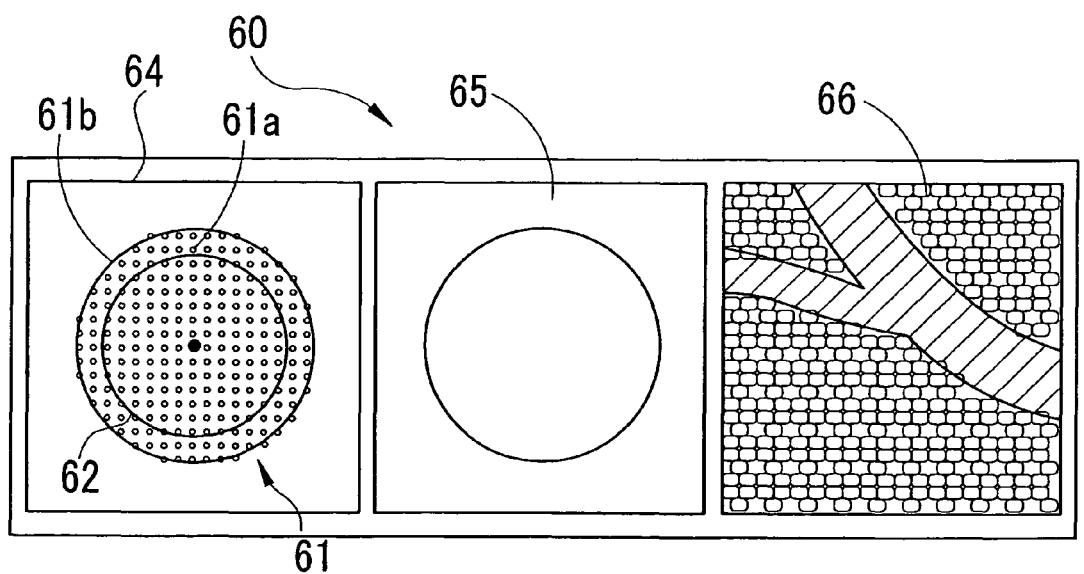
Figure 14A:
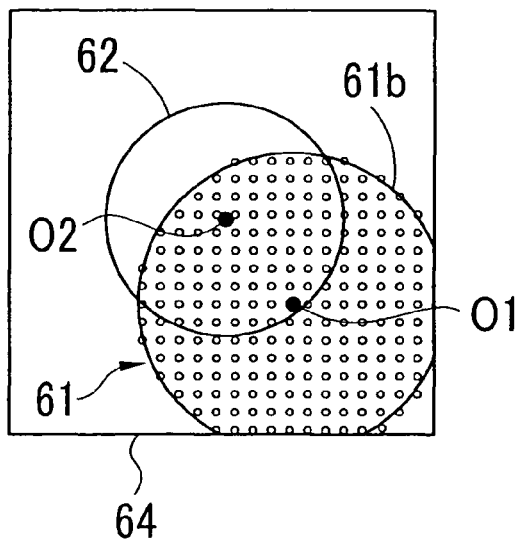
FIGS. 14A and MB are diagrams to explain a specific example of an effective region change.
Figure 14B:
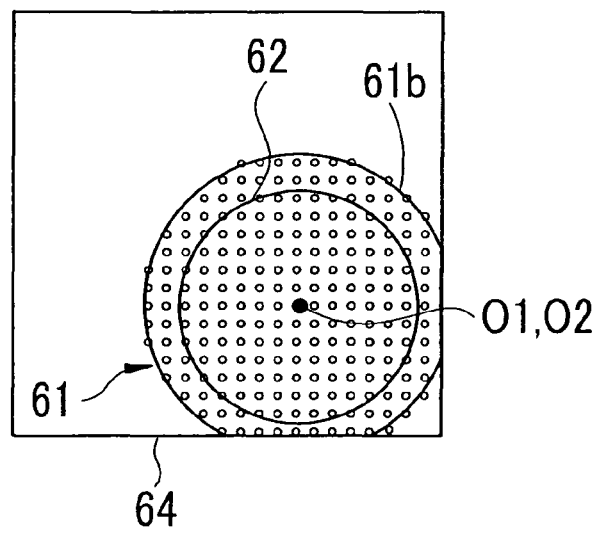

A specific example of the effective region change is described referring to FIGS. 14A and 14B. For example, the controller 80 calculates a central coordinate O1 of the Hartmann image 61 from the detected positional information of the Hartmann image outer periphery 61b, and also calculates a central coordinate O2 of the circle 62 (see FIG. 14A). The controller 80 changes the wavefront control position of the wavefront compensation device 72 so that the central coordinate O1 of the Hartmann image 61 and the central coordinate O2 of the circle 62 are positionally consistent with each other, thereby changing the position of the effective region 41. Accordingly, the circle 62 stays in the Hartmann image outer periphery 61b as illustrated in FIG. 14B, enabling the aberration correction. Further, referring to FIG. 12B, the aberration has been removed as illustrated in an aberration correction graphic 65, and an aberration-removed image is displayed as the cell image 66.

The examinee's eye is likely to move at all times. Therefore, the controller 80 makes the position of the effective region 41 of the wavefront compensation device 72 follow any changes of the measurable region relative to the measurement optical axis.

As the circle 62 is positionally adjusted, the controller 80 performs the aberration correction control in a second effective region after the positional adjustment using the aberration correction condition used in the first effective region before the positional adjustment. After the adjustment to the second effective region, the controller 80 performs as the aberration correction control a feedback control which repeats the aberration detection and wavefront compensation control based on the detection result. Thus, the aberration correction amount used in the effective region 41 before the positional adjustment is substituted for the aberration compensation amount for the effective region 41 after the positional adjustment. Then, the controller 80 changes the aberration correcting position while maintaining the aberration correction amount.

When the effective region 41 is positionally adjusted, for example, the controller 80 causes the storage unit 81 to store therein the aberration compensation amount before or immediately before the region formed by the circle 62 is positionally displaced from the region formed by the Hartmann image outer periphery 61b. As soon as the positional adjustment of the circle 62 is completed, the controller 80 makes the wavefront compensation device 72 operate based on the aberration compensation amount stored in the storage unit 81. The original aberration compensation amount is not necessarily kept in the storage unit. The original aberration compensation amount may be kept by any other means whenever the effective region is changed as far as the wavefront compensation device 72 is operated based on the aberration compensation amount reflecting thereon the aberration detection result before the region formed by the circle 62 is positionally displaced from the region formed by the Hartmann image outer periphery 61b, and a drive signal almost equal to a drive signal before the region formed by the circle 62 is positionally displaced from the region formed by the Hartmann image outer periphery 61b is applied thereto.

In the case of LCOS, the controller 80 positionally adjusts the effective region 41 and further adjusts a voltage to be applied to each pixel of the LCOS in the effective region 41 referring to an applied voltage before the region formed by the circle 62 is positionally displaced from the region formed by the Hartmann image outer periphery 61b so that an index of refraction of the LCOS is constant. In the case of a deformable mirror, as to the effective region, the controller 80 adjusts a voltage to be applied to each drive unit referring to an applied voltage before the region formed by the circle 62 is positionally displaced from the region formed by the Hartmann image outer periphery 61b so that an overall shape of the mirror is constant.

In the case where the positional displacement information is beyond the range of tolerance, the controller 80 operates the fundus photographing optical system 100 to continuously obtain fundus images with high magnifying powers and output the high-magnification images to the monitor 70 as moving images. Thus, the controller 80 performs a tracking control in which positional movement of the effective region of the wavefront compensation device 72 is used.

After the position of the circle 62 is adjusted, the controller 80 detects the wavefront aberration using the wavefront sensor 73 and transmits a drive signal based on the obtained aberration detection result to the wavefront compensation device 72. While the circle 62 is staying in the outer periphery 61b, the controller 80 causes the wavefront compensation device 72 to repeatedly perform the wavefront compensation based on the aberration detection/detection result obtained by the wavefront sensor 73. Accordingly, the aberration detection result obtained in real time is reflected on the wavefront compensation device 72. As a result, a good high-magnification fundus image hardly blurred is obtained.

When the wavefront aberration is thus compensated and a predetermined trigger signal is output, the fundus cell image is obtained as a moving image or a still image.

During the photographing operation, the position of the pupil of the examinee's eye may largely move, causing the Hartmann image 61 to be positionally displaced from the compensatable region 64 of the wavefront compensation device 72. When, for example, an alarm sound is emitted or a message notifying such a large positional movement of the examinee's eye is displayed on the screen of the monitor 70, the examiner can know that the position of the examinee's eye has largely moved. In that case, the examiner performs rough alignment again by positionally adjusting the jaw rest 610 so that the Hartmann Image 61 stays within the compensatable region 64 of the wavefront compensation device 72.

As described so far, whenever the pupil position of the examinee's eye moves making it impossible to obtain the aberration information of the examinee's eye E, the measurement position thereby displaced is corrected, and microscopic sites of the fundus are smoothly photographed with a good image quality. The examiner no longer has to pay attention to the positional alignment for any changes of the pupil position of the examinee's eye, largely reducing the examiner's burden.

Whenever the effective region is positionally changed, the feedback control for aberration compensation starts with the aberration compensation amount of the wavefront compensation device 72 before the need to positionally change the effective region arises, reducing an amount of time necessary for the aberration correction. As a result, a fundus image with a good image quality can be obtained in a time-efficient manner.

In determining the comparison result, the controller 80 may determine the comparison result as acceptable (OK) when the coordinates of all of the point image positions on the Hartmann image outer periphery 61b are located at the same position or on an outer side of the coordinates of the circle 62 and the region formed by the outer periphery of the Hartmann image 61 stays in the region formed by the outer periphery of the circle 62. The controller 80 may determine the comparison result as unacceptable (NG) in the case where the coordinates of the point image positions on the outer periphery of the Hartmann image 61 are located on an inner side of coordinates on an outer periphery of the circle 62.

In determining the comparison result, the index pattern image needs not fulfill the effective region by 100% as far as the wavefront aberration is measured with a certain accuracy (for example, 95% of the region). In the case where any displacement is detected in the determination result, the controller 80 controls the wavefront compensation device 72 to change the effective region so that the index pattern image can be received beyond a range of tolerance in the effective region (for example, by a certain ratio or more).

According to the present embodiment, the controller 80 detects information of the positional displacement between the effective region of the wavefront compensation device 72 and the detection region of the fundus reflected light flux by the wavefront sensor 73 based on the output signal of the wavefront sensor 73, however, the present embodiment is not necessarily limited thereto. The apparatus detects information of the positional displacement in the direction orthogonal to the optical axis between the effective region of the wavefront compensation device 72 and the wavefront measurement region.

For example, the apparatus is provided with an observation optical system which observes an anterior eye part front image of the examinee's eye. The controller 80 detects the position of pupil from the anterior eye part front image obtained by the observation optical system, and detects information of any positional displacement between the detected pupil position and the optical axis of the aberration detection optical system 110.

To detect the pupil position, for example, an effective region is set on an anterior eye part observation camera, and the controller 80 extracts an outer edge portion of pupil through an image process from the anterior eye part front image obtained by the anterior eye part observation system and detects the pupil position based on the extracted outer edge portion.

Further provided are; an alignment index projection optical system which projects an alignment light on the examinee's eye to form an alignment index in a peripheral portion of a cornea, and an alignment index detection optical system which detects the alignment index formed in the peripheral portion of the cornea. For example, an obtained alignment detection result and the displacement information are associated with each other beforehand by the anterior eye part observation system. Then, the controller 80 indirectly detects the pupil position through the detection result obtained by the alignment index detection optical system. In that case, the pupil position is indirectly detected under the assumption that a cornea peak position detected by the alignment index and a pupil center position of a human eye are substantially equal.

The present embodiment changes the effective region and also changes the compensation amount of the newly obtained effective region to the aberration compensation amount of the original effective region, however, is not necessarily limited thereto. For example, the aberration detection starts after the effective region is changed to start the whole compensation process again.

According to the present embodiment, the controller 80 may retain the aberration-corrected condition before the effective region is changed in place of resetting the aberration compensation amount in the pre-change effective region to zero.

This reduces a drive amount and a drive time when the wavefront compensation device 72 is driven in the case where the effective region returns to its original position, capturing a favorable fundus image in a time-efficient manner. After the effective region is changed, the wavefront compensation device 72 may be reset to an initial state before the aberration detection started.

The present embodiment changes the effective region and then continuously performs the feedback control after the aberration compensation amount before the displacement information goes beyond the range of tolerance is reflected on the aberration compensation amount of the wavefront compensation device 72, however is not necessarily limited thereto.

In the case where a center position of the measurable region deviates from a near region of a detection optical axis L1 of the aberration detection optical system 110, the controller 80, for example, moves the effective region 41 reflecting thereon the aberration compensation and temporarily suspends the feedback control, and then restarts the feedback control when the center position of the measurable region returns to the near region of the detection optical axis L1.

For example, the controller 80 makes the storage unit 81 store therein the aberration compensation amount in the effective region 41 of the wavefront aberration compensation device 72 before the occurrence of any positional displacement. When the center position of the measurable region returns to the near region of the detection optical axis L1, the controller 80 returns the effective region 41 to its original position and makes the aberration compensation amount stored in the storage unit 81 be reflected on the wavefront compensation device 72.

Figure 15:
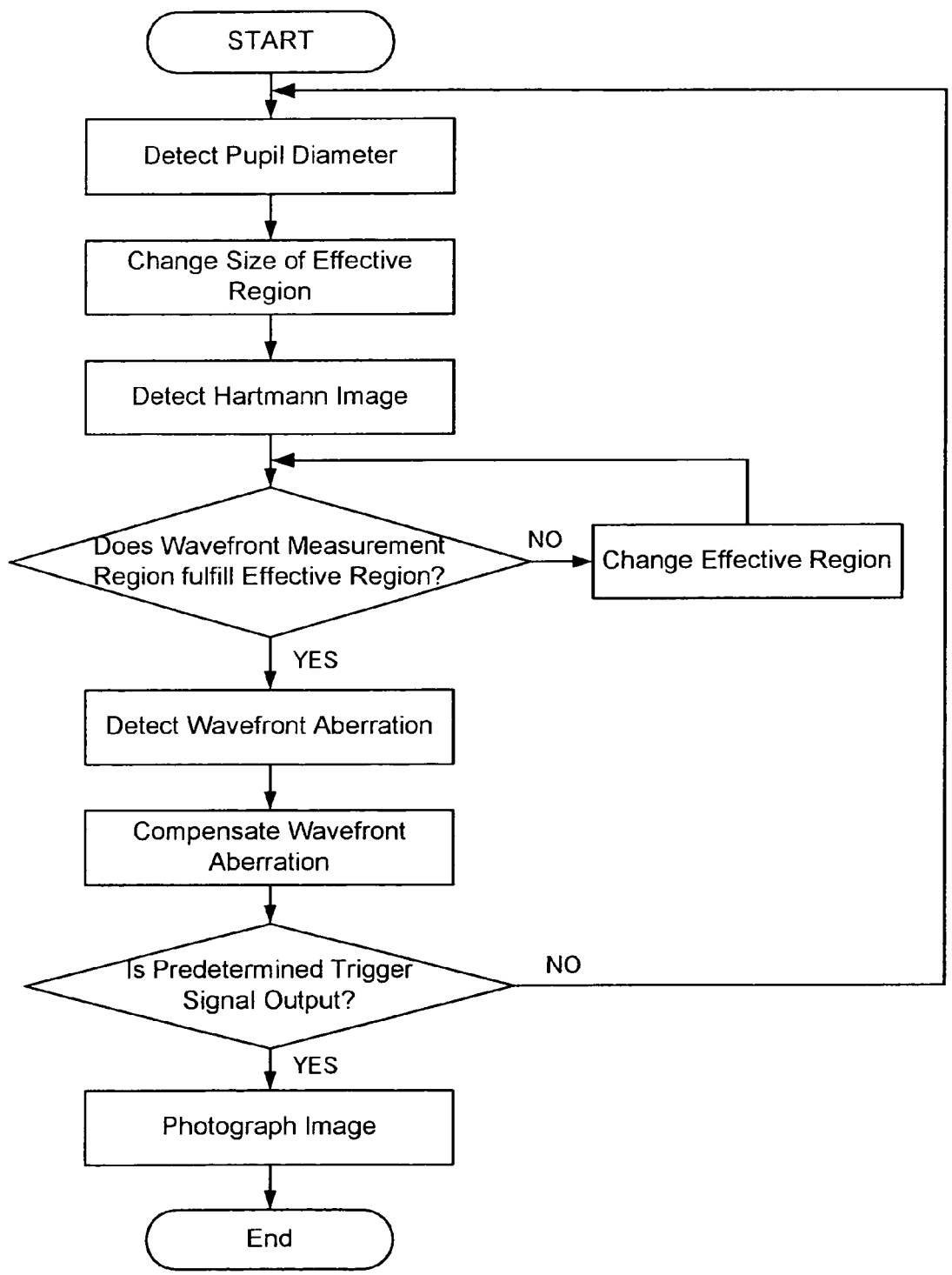
FIG. 15 is a flowchart to explain operations in a third embodiment.

Finally, a third embodiment of the fundus photographing apparatus is hereinafter described. The third embodiment is characterized in that the first and second embodiments are combined. According to the third embodiment, as illustrated in FIG. 15, the effective region is resized (corrected) depending on the Hartmann image size, and any positional displacement between the wavefront measurement region and the wavefront compensation device 72 is corrected.

For example, the controller 80 resizes (corrects) the effective region. After the effective region is resized, the controller 80 corrects any positional displacement between the wavefront measurement region and the effective region of the wavefront compensation device 72. The first and second embodiments are referenced for a specific control operation.

Accordingly, the aberration correction can be more accurate because the positional displacement of the pupil is corrected after the pupil size is corrected. In the case where the aberration information of the eye E is no longer detectable after the pupil size or the pupil position of the examinee's eye changed, the positional displacement is still correctable. As a result, microscopic sites of the fundus are smoothly photographed with a good image quality.

In place of correcting the positional displacement between the wavefront measurement region and the effective region of the wavefront compensation device 72 after the effective region is resized, the displacement may be corrected before resizing.

The resizing and displacement correction of the effective region described so far may be performed when the pupil size and displacement information continuously detected exceed predetermined threshold values or may be performed at given time intervals.

The fundus photographing optical system 100 described so far is a confocal optical system (SLO optical system) which receives light flux reflected from fundus of the examinee's eye through a confocal opening located at a position substantially conjugate with the fundus of the examinee's eye to photograph a confocal front image of the fundus of the examinee's eye, however, is not necessarily limited thereto (for example, see PCT Application National Publication 2001-507258).

Such an optical system may be replaced with a fundus camera optical system which receives light flux reflected from fundus of the examinee's eye through a two-dimensional imaging device to capture a fundus front image of the examinee's eye or an optical coherence tomography optical system (OCT optical system) which receives light flux reflected from fundus of the examinee's eye and an interference light generated by a reference light to obtain a tomographic image of the examinee's eye.

The invention claimed is:

1. A fundus photographing apparatus with wavefront compensation, including:
a fundus photographing optical system for capturing a fundus image by receiving a reflected light from fundus of an examinee's eye;
a wavefront compensation device placed in an optical path of the fundus photographing optical system to compensate a wavefront aberration of the examinee's eye by controlling an incident light wavefront;
a wavefront aberration detection optical system for projecting a measurement light on the fundus of the examinee's eye to detect a reflected light of the measurement light from the fundus using a wavefront sensor; and
a controller for controlling an effective region formed on the wavefront compensation device so as to correct a difference between the effective region formed on the wavefront compensation device where an aberration correction control is effective and a wavefront measurement region of the wavefront aberration detection optical system where the wavefront aberration is measured.

2. The fundus photographing apparatus with wavefront compensation according to claim 1, wherein information of pupil of the examinee's eye is obtained, and the difference includes a difference between sizes of the obtained pupil information and the effective region of the wavefront compensation device.

3. The fundus photographing apparatus with wavefront compensation according to claim 2, further including:
a detector for receiving the reflected light from the examinee's eye; and
a pupil detector for detecting the pupil information of the examinee's eye based on a light reception signal output from the detector,
wherein the controller obtains the pupil information of the examinee's eye from the pupil detector.

4. The fundus photographing apparatus with wavefront compensation according to claim 3, further including an anterior eye part observation unit for capturing an anterior eye part image of the examinee's eye,
wherein the pupil detector extracts an outer edge portion of the pupil through an image process from the anterior eye part image captured by the anterior eye part observation unit to detect a pupil diameter, and
wherein the controller resizes the effective region depending on the pupil diameter detected by the pupil detector.

5. The fundus photographing apparatus with wavefront compensation according to claim 3,
wherein the pupil detector detects an outer edge portion in a light reception region of an index pattern image obtained by the wavefront sensor, and
wherein the controller resizes the effective region depending on a size of the outer edge portion detected by the pupil detector.

6. The fundus photographing apparatus with wavefront compensation according to claim 3,
wherein the pupil detector calculates a center position in the light reception region of the index pattern image from the detected outer edge portion to detect a dimension from a central coordinate of the center position to the outer edge portion, and
wherein the controller resizes the effective region depending on the dimension from the central coordinate to the outer edge portion detected by the detector.

7. The fundus photographing apparatus with wavefront compensation according to claim 3, wherein the controller performs a first feedback control which obtains the pupil information of the examinee's eye and resizes the effective region depending on any changes of the obtained pupil information.

8. The fundus photographing apparatus with wavefront compensation according to claim 3, wherein the controller performs a second feedback control which detects the wavefront aberration of the examinee's eye based on a detection signal output from the wavefront sensor and controls the wavefront compensation device based on an obtained detection result.

9. The fundus photographing apparatus with wavefront compensation according to claim 2, wherein the difference includes a displacement between the effective region of the wavefront compensation device and the wavefront measurement region of the wavefront aberration detection optical system in a direction orthogonal to an optical axis direction.

10. The fundus photographing apparatus with wavefront compensation according to claim 1, wherein the difference includes a displacement between the effective region of the wavefront compensation device and the wavefront measurement region of the wavefront aberration detection optical system in a direction orthogonal to an optical axis direction.

11. The fundus photographing apparatus with wavefront compensation according to claim 10, further including a displacement detector for detecting information of the displacement between the effective region and the wavefront measurement region in the direction orthogonal to the optical axis,
wherein in the case where the displacement information detected by the displacement detector goes beyond a range of tolerance, the controller positionally adjusts the effective region so that the displacement information stays within the range of tolerance.

12. The fundus photographing apparatus with wavefront compensation according to claim 11, wherein when the effective region is positionally adjusted, the controller performs the aberration correction control in a second effective region after the positional adjustment using an aberration-corrected condition used in a first effective region before the positional adjustment.

13. The fundus photographing apparatus with wavefront compensation according to claim 12, wherein after the adjustment to the second effective region, the controller performs a feedback control which repeatedly performs the aberration detection and a wavefront compensation control based on an obtained detection result.

14. The fundus photographing apparatus with wavefront compensation according to claim 11, wherein the displacement information detected by the displacement detector is information of a displacement between the effective region of the wavefront compensation device set on the wavefront sensor and a light reception region of a light flux of the reflected light from the fundus detected by the wavefront sensor.

15. The fundus photographing apparatus with wavefront compensation according to claim 11, further including:
an observation optical system for observing an anterior eye part front image of the examinee's eye; and
a pupil detector for detecting a pupil position from the anterior eye part front image captured by the observation optical system,
wherein the displacement information detected by the detector is information of a displacement between the pupil position detected by the pupil detector and an optical axis of the wavefront aberration detection optical system.

16. The fundus photographing apparatus with wavefront compensation according to claim 15, wherein the pupil detector extracts an outer edge portion of the pupil through an image process from the anterior eye part front image captured by the observation optical system and detects the pupil position based on the extracted outer edge portion.

17. The fundus photographing apparatus with wavefront compensation according to claim 15, further including:
an alignment index projection optical system for projecting an alignment light on the examinee's eye to form an alignment index in a peripheral portion of a cornea; and
an alignment index detection optical system for detecting the alignment index formed in the peripheral portion of the cornea,
wherein the pupil detector detects the pupil position based on a detection result obtained by the alignment index detection optical system.

* * * * *